(12) United States Patent
Jackson

(10) Patent No.: US 10,702,309 B2
(45) Date of Patent: *Jul. 7, 2020

(54) PIVOTAL BONE ANCHOR ASSEMBLY WITH MULTI-PART SHANK RETAINER AND ROD-ENGAGING INSERT

(71) Applicant: Roger P. Jackson, Prairie Village, KS (US)

(72) Inventor: Roger P. Jackson, Prairie Village, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/544,325

(22) Filed: Aug. 19, 2019

(65) Prior Publication Data

US 2019/0365428 A1 Dec. 5, 2019

Related U.S. Application Data

(63) Continuation-in-part of application No. 16/148,594, filed on Oct. 1, 2018, now Pat. No. 10,398,474, which (Continued)

(51) Int. Cl.
*A61B 17/70* (2006.01)

(52) U.S. Cl.
CPC ...... *A61B 17/7035* (2013.01); *A61B 17/7032* (2013.01); *A61B 17/7037* (2013.01); *A61B 17/7011* (2013.01)

(58) Field of Classification Search
CPC .............. A61B 17/7037; A61B 17/704; A61B 17/7031; A61B 17/7008; A61B 17/7085;

(Continued)

(56) References Cited

U.S. PATENT DOCUMENTS 4,686,835 A 8/1987 Alsenz
5,257,993 A 11/1993 Asher et al.
(Continued)

OTHER PUBLICATIONS

International Search Report and Written Opinion PCT/US2015/056706, dated Jan. 6, 2016.
(Continued)

*Primary Examiner* — Pedro Philogene
(74) *Attorney, Agent, or Firm* — Polsinelli PC

(57) ABSTRACT

A polyaxial bone screw assembly includes a threaded shank body having an upper capture structure, a head and a multi-piece retainer, articulation structure. The geometry of the retainer structure pieces corresponds and cooperates with the external geometry of the capture structure to frictionally envelope the retainer structure between the capture structure and an internal surface defining a cavity of the head. The head has a U-shaped cradle defining a channel for receiving a spinal fixation or stabilization longitudinal connecting member. The head channel communicates with the cavity and further with a restrictive opening that receives retainer pieces and the capture structure into the head but prevents passage of frictionally engaged retainer and capture structures out of the head. The retainer structure includes a substantially spherical surface that mates with the internal surface of the head, providing a ball joint, enabling the head to be disposed at an angle relative to the shank body. Methods of installation are also provided.

44 Claims, 14 Drawing Sheets

Related U.S. Application Data is a continuation of application No. 15/617,614, filed on Jun. 8, 2017, now Pat. No. 10,085,774, which is a continuation of application No. 15/095,022, filed on Apr. 9, 2016, now Pat. No. 9,700,354, which is a continuation of application No. 12/930,768, filed on Jan. 14, 2011, now Pat. No. 9,320,545, which is a continuation of application No. 12/080,202, filed on Apr. 1, 2008, now Pat. No. 7,875,065, which is a continuation-in-part of application No. 11/281,818, filed on Nov. 17, 2005, now Pat. No. 7,625,396.

(60) Provisional application No. 60/630,478, filed on Nov. 23, 2004.

(58) Field of Classification Search
CPC .............. A61B 17/708; A61B 17/7091; A61B 17/7055; A61B 17/7011; A61B 17/7032; A61B 17/7035
USPC ......... 606/246–279, 300–328; 411/353, 533, 411/922, 81
See application file for complete search history.

(56) References Cited

U.S. PATENT DOCUMENTS

| | | | |
|---|---|---|---|
| 5,545,165 A | 8/1996 | Biedermann et al. | |
| 5,716,356 A | 2/1998 | Biedermann et al. | |
| 5,720,751 A | 2/1998 | Jackson | |
| 5,873,878 A | 2/1999 | Harms et al. | |
| 5,910,141 A | 6/1999 | Morrison et al. | |
| 6,077,262 A | 6/2000 | Schlapfer et al. | |
| 6,440,133 B1 | 8/2002 | Beale et al. | |
| 6,540,749 B2 | 4/2003 | Schafer et al. | |
| 6,565,565 B1 | 5/2003 | Yuan et al. | |
| 6,648,888 B1 | 11/2003 | Shluzas | |
| 6,660,006 B2 | 12/2003 | Markworth et al. | |
| 6,905,500 B2 | 6/2005 | Jeon et al. | |
| 7,179,261 B2 | 2/2007 | Sicvol et al. | |
| 7,250,052 B2 | 7/2007 | Landry et al. | |
| 7,476,228 B2 | 1/2009 | Abdou | |
| 7,503,924 B2 | 3/2009 | Lee et al. | |
| 7,559,943 B2 | 7/2009 | Mujwid | |
| 7,618,440 B2 | 11/2009 | Gray et al. | |
| 7,618,444 B2 | 11/2009 | Shluzas | |
| 7,625,396 B2 * | 12/2009 | Jackson | A61B 17/7037 606/266 |
| 7,641,670 B2 | 1/2010 | Davison et al. | |
| 7,691,132 B2 * | 4/2010 | Landry | A61B 17/1604 606/279 |
| 7,736,305 B2 | 6/2010 | DiPoto | |
| 7,776,040 B2 | 8/2010 | Markworth et al. | |
| 7,815,650 B2 | 10/2010 | Shluzas et al. | |
| 7,862,587 B2 | 1/2011 | Jackson | |
| 7,862,588 B2 * | 1/2011 | Abdou | A61B 17/7035 606/246 |
| 7,875,065 B2 * | 1/2011 | Jackson | A61B 17/7035 606/305 |
| 8,034,086 B2 | 1/2011 | Iott et al. | |
| 7,887,539 B2 | 2/2011 | Dunbar et al. | |
| 7,955,355 B2 | 6/2011 | Chin | |
| 7,985,242 B2 | 7/2011 | Forton et al. | |
| 8,002,798 B2 | 8/2011 | Chin et al. | |
| 8,048,126 B2 | 11/2011 | Altarac et al. | |
| 8,105,361 B2 | 1/2012 | Anderson et al. | |
| 8,273,089 B2 | 9/2012 | Jackson | |
| 8,308,782 B2 * | 11/2012 | Jackson | A61B 17/7008 606/305 |
| 8,475,495 B2 | 7/2013 | Iott et al. | |
| 8,709,051 B2 | 4/2014 | Hammer et al. | |
| 8,840,652 B2 * | 9/2014 | Jackson | A61B 17/7008 606/305 |
| 9,320,545 B2 * | 4/2016 | Jackson | A61B 17/7035 |
| 9,522,021 B2 | 12/2016 | Jackson | |
| 9,629,669 B2 | 4/2017 | Jackson | |
| 9,700,354 B2 * | 7/2017 | Jackson | A61B 17/7035 |
| 9,987,054 B2 | 6/2018 | Jackson | |
| 10,039,577 B2 | 8/2018 | Jackson | |
| 10,085,774 B2 * | 10/2018 | Jackson | A61B 17/7035 |
| 10,398,474 B2 * | 9/2019 | Jackson | A61B 17/7035 606/305 |
| 2002/0161368 A1 | 10/2002 | Foley et al. | |
| 2003/0158552 A1 | 8/2003 | Jeon | |
| 2005/0065517 A1 | 3/2005 | Chin | |
| 2005/0192589 A1 | 9/2005 | Raymond et al. | |
| 2005/0277928 A1 | 12/2005 | Boschert | |
| 2008/0009864 A1 | 1/2008 | Forton et al. | |
| 2008/0077139 A1 | 3/2008 | Landry et al. | |
| 2008/0161853 A1 * | 7/2008 | Arnold | A61B 17/7004 606/246 |
| 2018/0250039 A1 | 9/2018 | Jackson | |
| 2018/0289400 A1 | 10/2018 | Jackson | |
| 2018/0317978 A1 | 11/2018 | Jackson | |

OTHER PUBLICATIONS

International Preliminary Report on Patentability regarding PCT/US2015/056706, dated Nov. 17, 2016.

\* cited by examiner

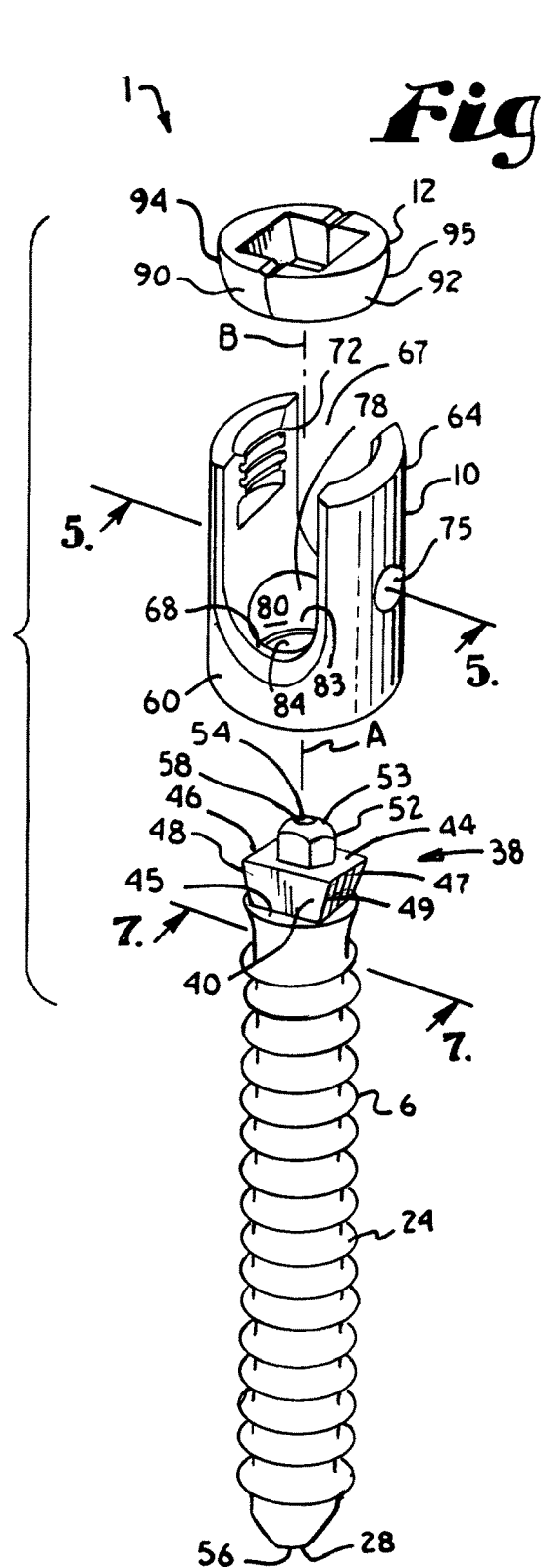
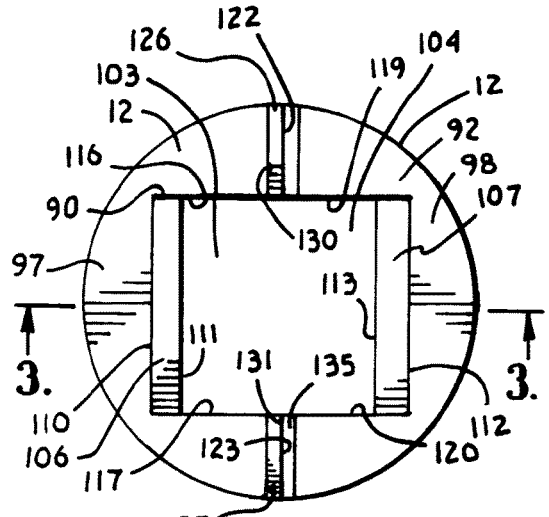
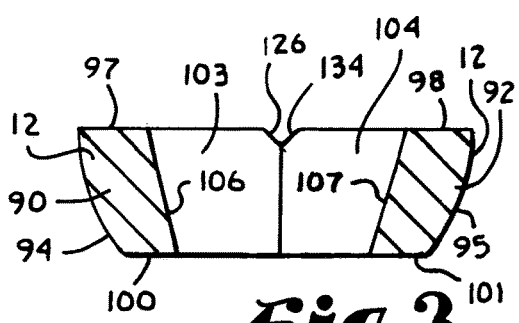
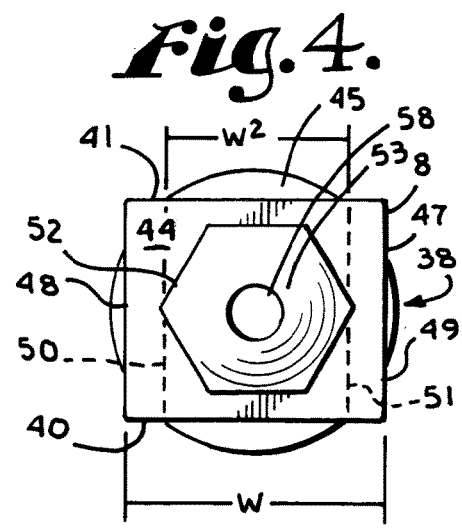

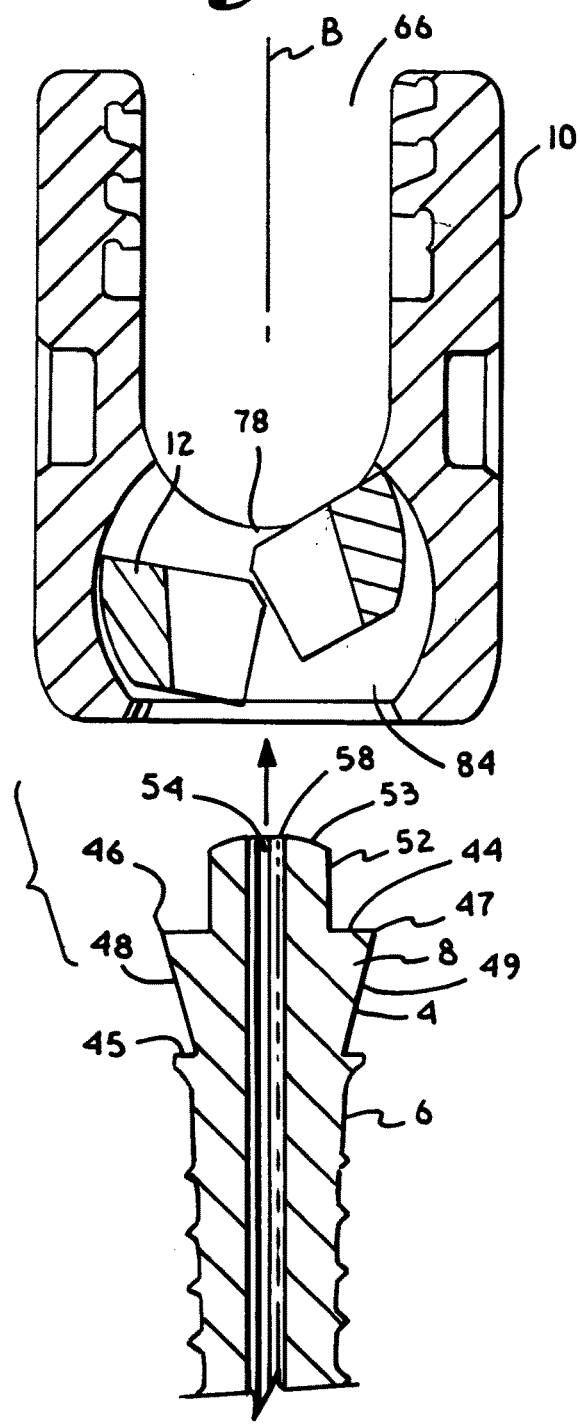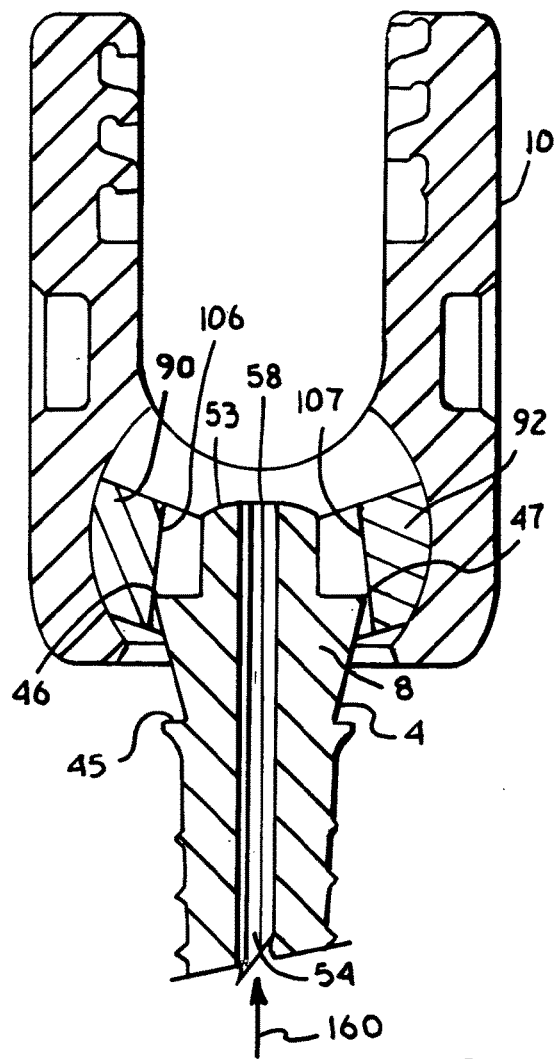

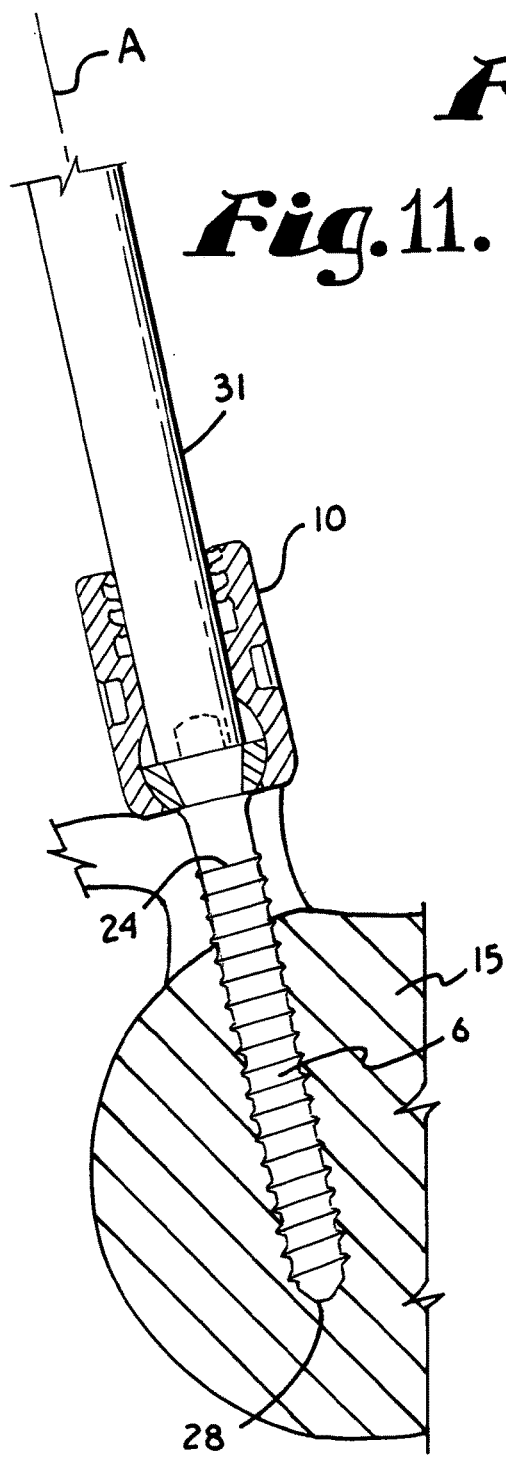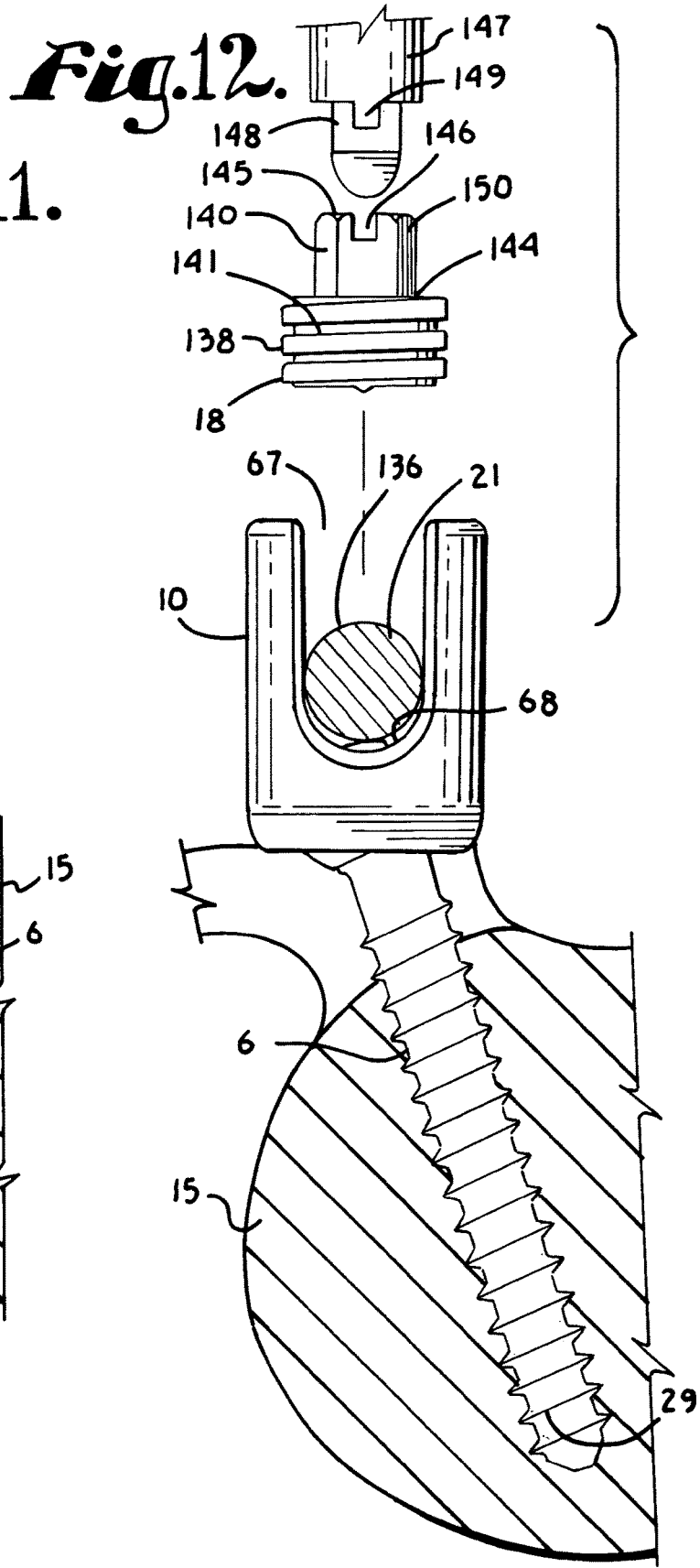

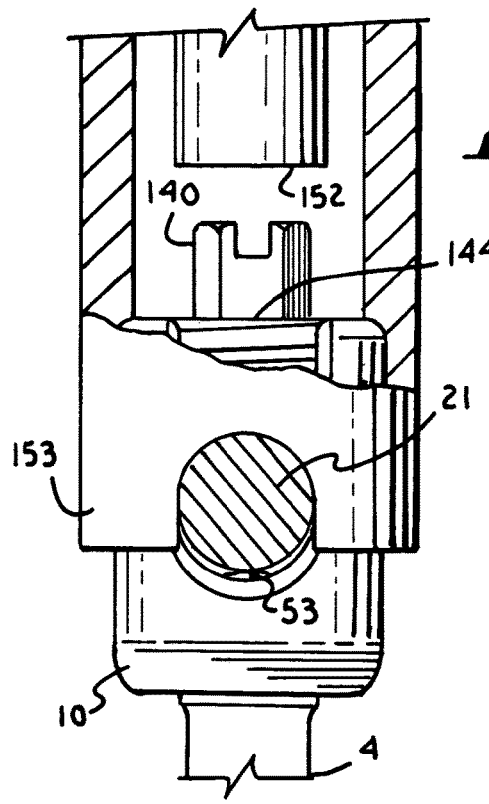
Fig. 14.
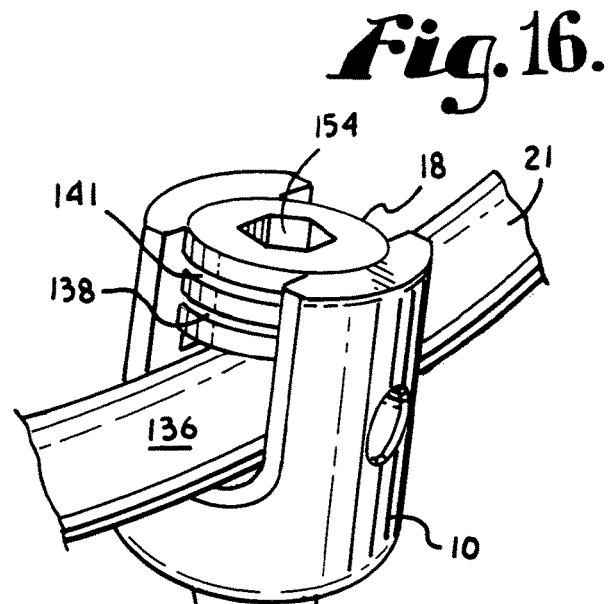
Fig. 16.
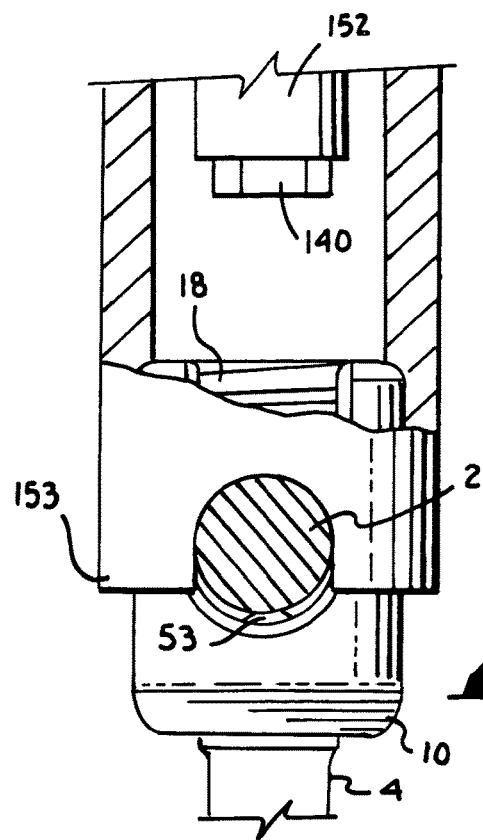
Fig. 15.
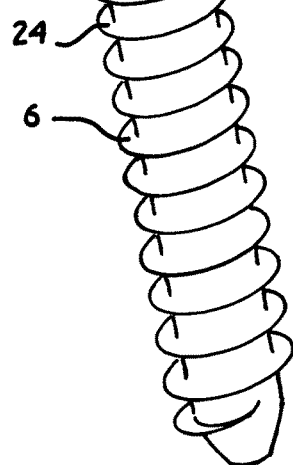

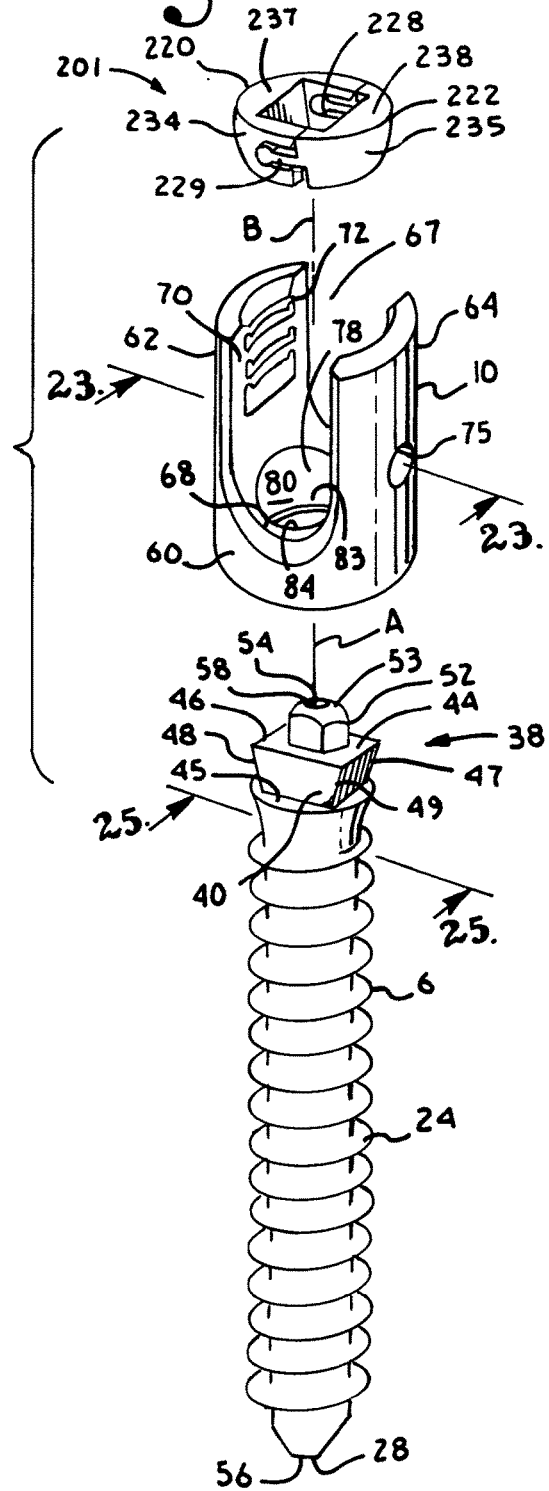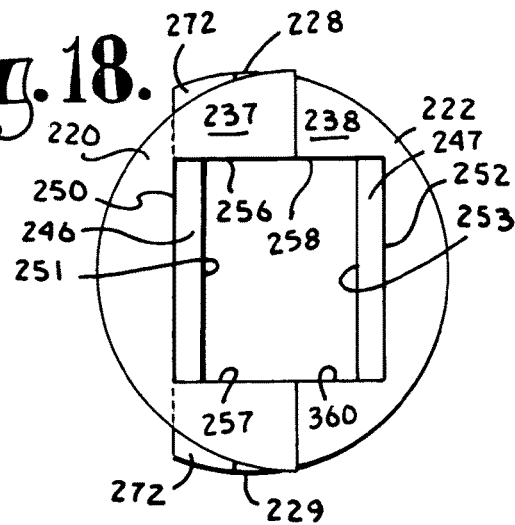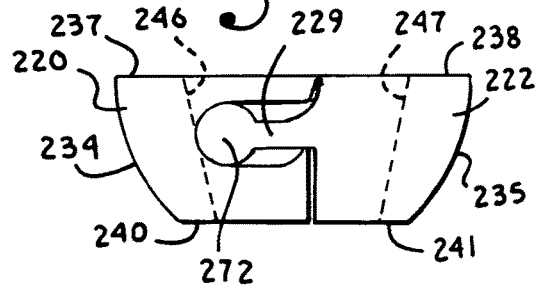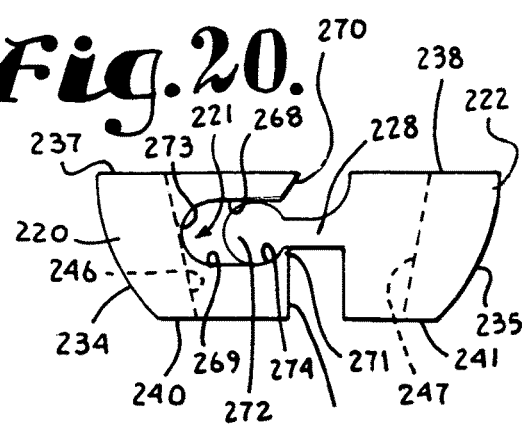

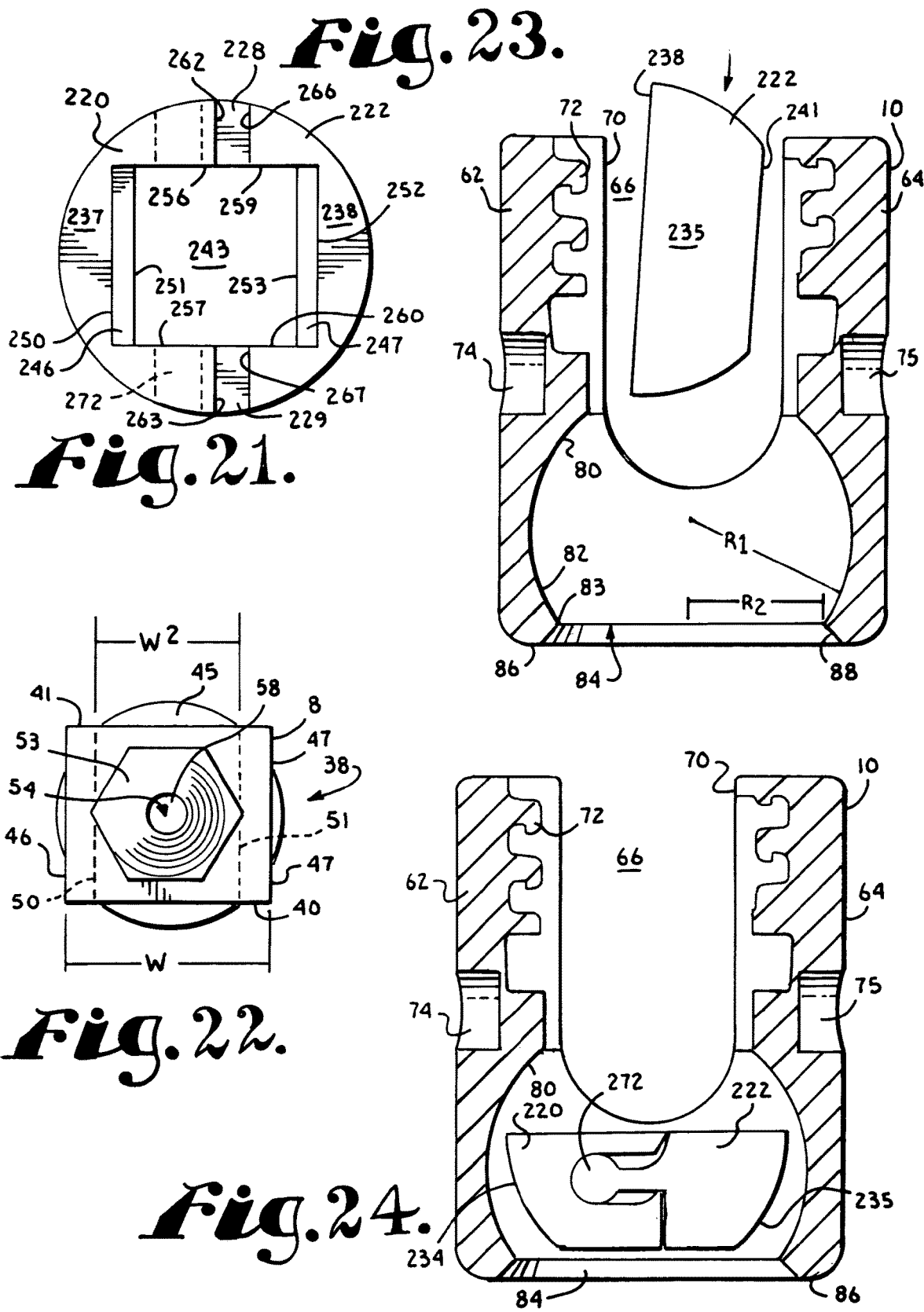

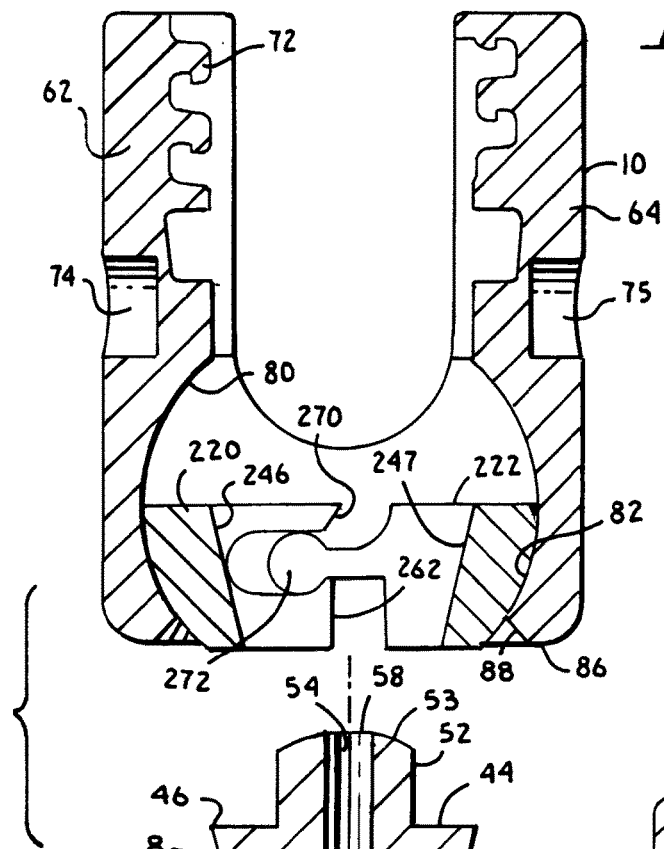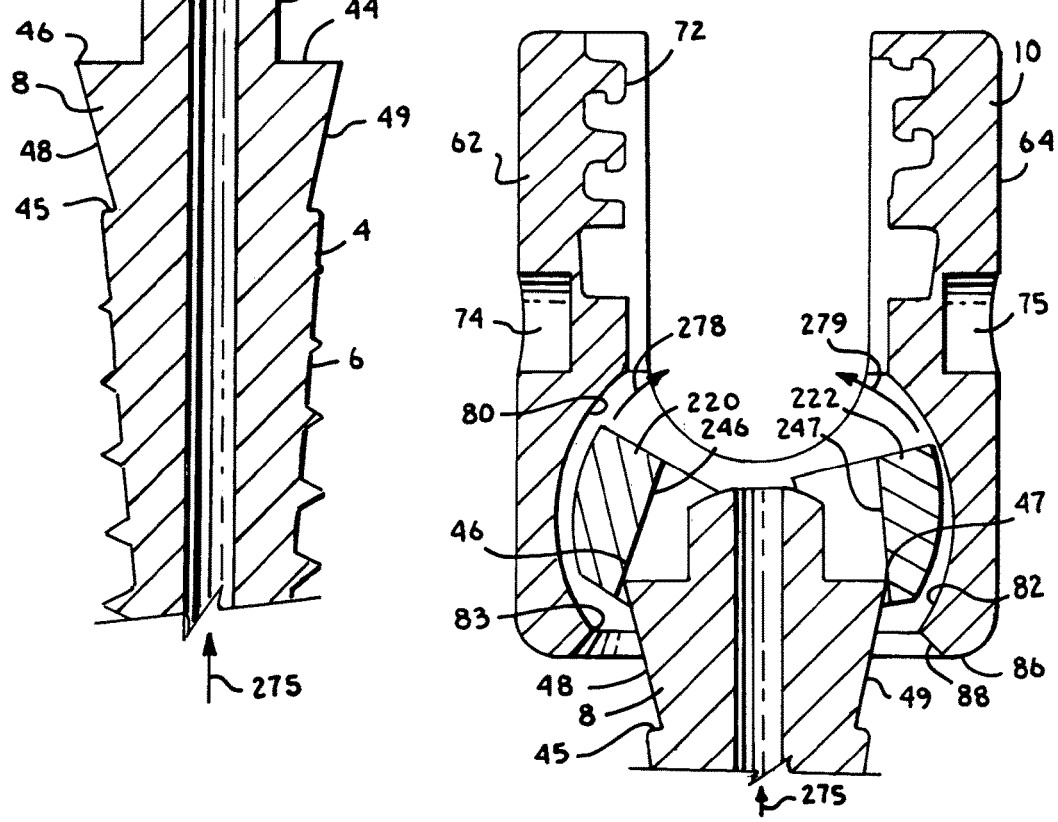

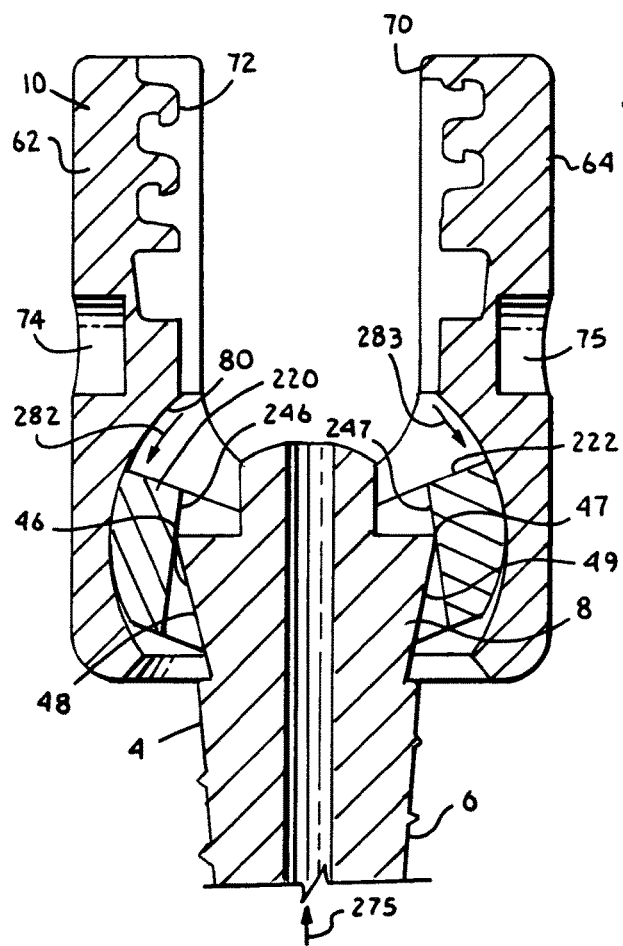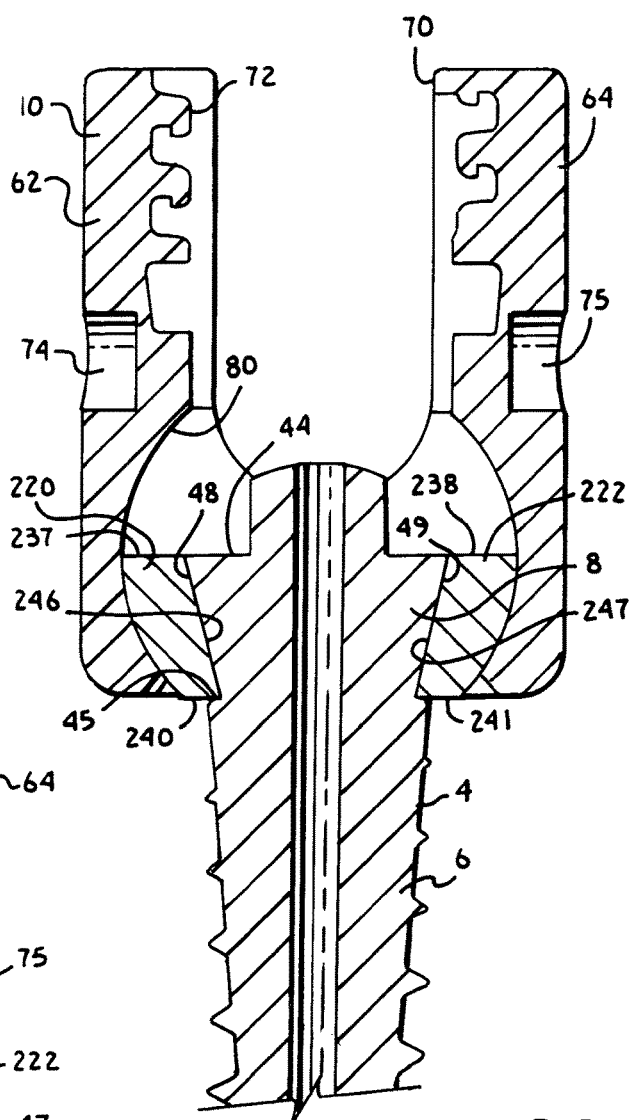

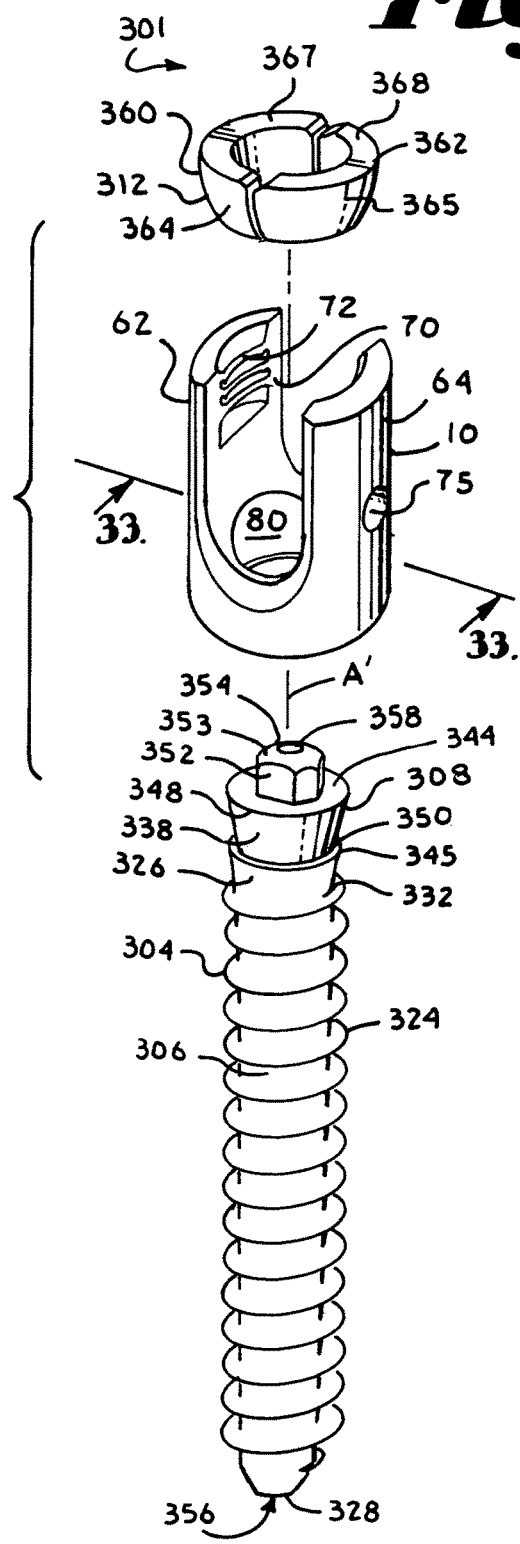
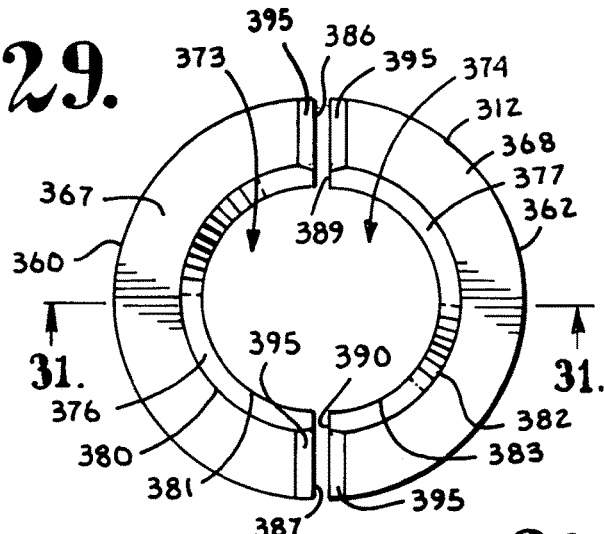
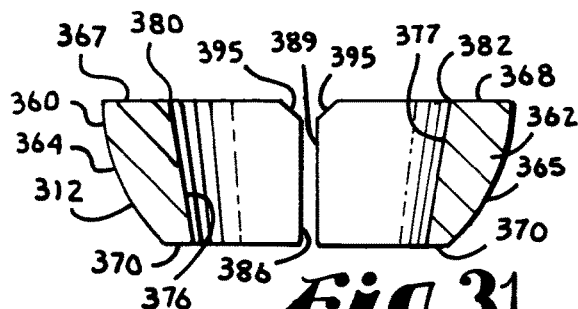
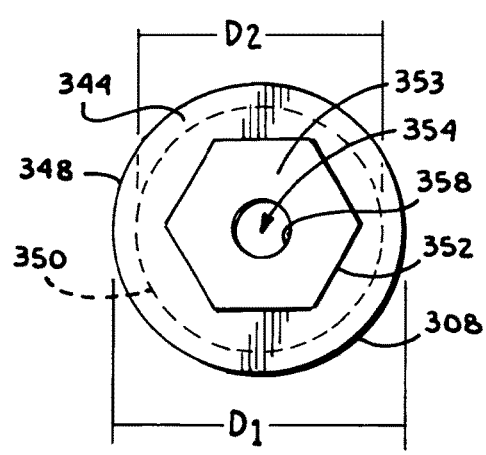

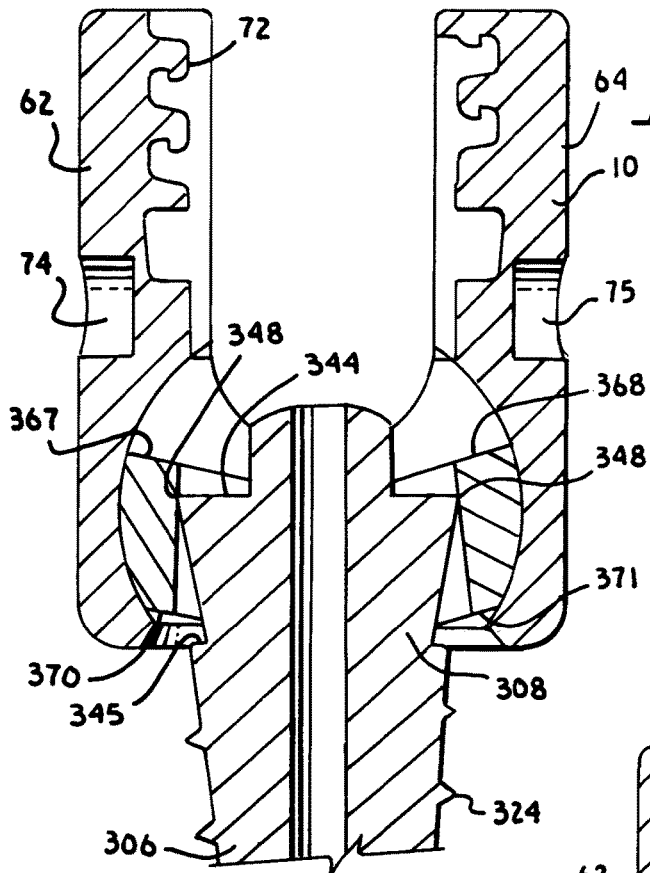
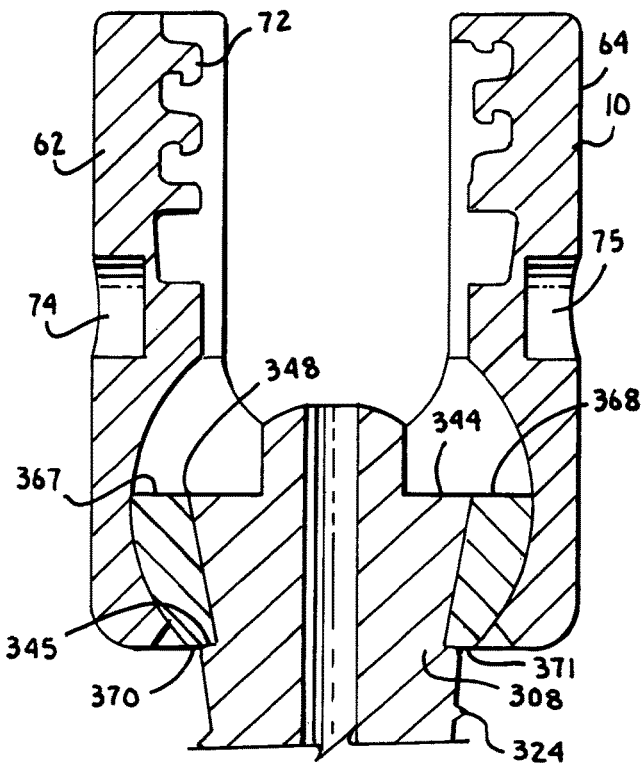

PIVOTAL BONE ANCHOR ASSEMBLY WITH MULTI-PART SHANK RETAINER AND ROD-ENGAGING INSERT

CROSS REFERENCE TO RELATED APPLICATIONS

This application is a continuation-in-part of U.S. patent application Ser. No. 16/148,594, filed Oct. 1, 2018, which is a continuation of U.S. patent application Ser. No. 15/617,614, filed Jun. 8, 2017, now U.S. Pat. No. 10,085,774, which is a continuation of U.S. patent application Ser. No. 15/095,022, filed Apr. 9, 2016, now U.S. Pat. No. 9,700,354, which is a continuation of U.S. patent application Ser. No. 12/930,768, filed Jan. 14, 2011, now U.S. Pat. No. 9,320,545, which is a continuation of U.S. patent application Ser. No. 12/080,202, filed Apr. 1, 2008, now U.S. Pat. No. 7,875,065, which is a continuation-in-part of U.S. patent application Ser. No. 11/281,818, filed Nov. 17, 2005, now U.S. Pat. No. 7,625,396, which claims the benefit of U.S. Provisional Application No. 60/630,478, filed Nov. 23, 2004, each of which is incorporated by reference in its entirety herein, and for all purposes.

BACKGROUND OF THE INVENTION

The present invention is directed to polyaxial bone screws for use in bone surgery, particularly spinal surgery. Such screws have a head that can swivel about a shank of the bone screw, allowing the head to be positioned in any of a number of angular configurations relative to the shank.

Many spinal surgery procedures require securing various implants to bone and especially to vertebrae along the spine. For example, elongate rods are often utilized that extend along the spine to provide support to vertebrae that have been damaged or weakened due to injury or disease. Such rods must be supported by certain vertebrae and support other vertebrae.

The most common mechanism for providing vertebral support is to implant bone screws into certain bones which then in turn support a rod or are supported thereby. Bone screws of this type may have a fixed head relative to a shank thereof. In the fixed bone screws, the head cannot be moved relative to the shank and the rod must be favorably positioned in order for it to be placed within the head. This is sometimes very difficult or impossible to do. Therefore, polyaxial bone screws are commonly preferred.

Polyaxial bone screws allow rotation of the head about the shank until a desired rotational position of the head is achieved relative to the shank. Thereafter, a rod can be inserted into the head and eventually the head is locked or fixed in a particular position relative to the shank.

A variety of polyaxial or swivel-head bone screw assemblies are available. One type of bone screw assembly includes an open head that allows for ease in placement of a rod within the head. A closure top or plug is then used to capture the rod in the head of the screw.

Because such implants are for placement within the human body, it is desirable for the implant to have as little effect on the body as possible. Consequently, heavy, bulky implants are undesirable and lighter implants with a relatively small profile both in height and width are more desirable. However, a drawback to smaller, lighter implants is that they may be more difficult to rigidly fix to each other and into a desired position. Lack of bulk may also mean lack of strength, resulting in slippage under high loading.

A drawback of some implants is that in an effort to provide an open, swivel head screw that is easy to assemble, the interior of the bone screw head is largely hollowed out, resulting in a cavity that may provide adequate space for the attachment of component parts within the cavity, but also may result in a head of reduced mass and thus possibly of reduced strength. If the head cavity size is reduced to maintain adequate bulk and strength of the head, the other bone screw components utilized to attach the shank to the head must be reduced in size or otherwise reconfigured, potentially resulting in bone screw shank components of lesser strength. Another potential difficulty is lack of working space for utilizing manipulating or fastening tools to attach the component parts to one another.

Furthermore, certain part configurations and/or reduced sizing of the component parts may result in limitations on the frictional, load bearing surfaces within the screw head once the screw is implanted on a vertebra and the head is fixed in a set angle with respect to the shank body. For example, a select portion of the interior of the head may be removed to create a recess so that other component parts of adequate bulk may be inserted in the head. This may result in excessive local pressure on other surfaces of the head after shank installation, which in turn may lead to localized damage and eventual loosening or deformation of the component parts. It is therefore desirable to draw a balance between mass and strength of the individual bone screw component parts, number of component parts, the configuration thereof, and ease of installation of the implant component parts to each other and to the vertebrae.

SUMMARY OF THE INVENTION

A polyaxial bone screw assembly according to the invention includes a shank with a capture structure loadable into a head, and a capture structure retaining and articulating structure that includes more than one discrete piece, each piece engageable with the capture structure and slidably engageable with the head.

The shank has an elongate body, a driving tip and a capture structure, the body disposed between the driving tip and the capture structure. The shank body is configured for fixation to a bone. The capture structure is a polyhedral or inverted conical formation having an edge spaced from the shank body and an oblique surface disposed between the edge and the body, the surface sloping in a direction toward the driving tip. In a first embodiment, the capture structure is a polyhedron and includes front and back surfaces that are trapezoidal, and two oblique surfaces that are rectangular. In an alternative embodiment, the capture structure oblique surface is conical.

The polyaxial bone screw head includes a top portion and a base. The head top portion defines an open channel. The base has a seating surface partially defining a cavity, the channel communicating with the cavity, and the cavity communicating with an exterior of the base through an opening sized and shaped to receive the capture structure therethrough.

The retainer structure includes at least two and up to a plurality of discrete parts or pieces, each part or piece having an inner surface and an outer surface. Each inner surface of the retainer structure is configured to be in frictional engagement with an outer surface of the capture structure and each outer surface of the retainer structure is configured to be in slidable engagement with the seating surface in the base of the screw head. One illustrated embodiment of a retainer structure according to the invention is a discrete two-part or piece structure, with the pieces being substantial mirror images of one another. The two pieces preferably are in contact when fully installed in a bone screw head. In another illustrated embodiment according to the invention, first and second retainer structure pieces are connectable to one another, with a first piece forming a recess and the second piece having a projection that is receivable in the recess. The projection is slidable within the recess, allowing for telescoping of the structure during insertion into a bone screw head and also some rotation or jointed movement between the first and second pieces after insertion into the bone screw head, and particularly during subsequent insertion of the shank into the head. Upon full installment in the bone screw head, portions of the first and second pieces are in spaced relation with each other. In other embodiments according to the invention, two or more discrete retainer pieces remain un-attached to one another when fully installed and operational in the polyaxial bone screw head, and may be disposed in contact with or in spaced relation to one another.

Both the multi-part retainer structure outer surface and the head seating surface are preferably substantially spherical. In one embodiment according to the invention, both the multi-part retainer structure inner surface and the capture structure oblique surface are planar. In another embodiment, each retainer structure part has an inner surface that is curved and the capture structure oblique surface is conical.

In an embodiment according to the invention in which the capture structure oblique surface is planar, the capture structure also has a second oblique surface and front and rear parallel surfaces. First and second inner walls of a retainer structure part are frictionally engageable with the front and rear surfaces, respectively. Furthermore, in such an embodiment the retainer structure preferably includes first and second discrete parts, the second retainer structure part is a substantial mirror image of the first retainer structure part, with both retainer structure parts having first and second inner walls that frictionally cooperate with the front and rear parallel surfaces of the capture structure, as well as first and second sloping surfaces that frictionally engage the oblique surfaces of the capture structure.

The capture structure may also include a tool engagement formation disposed thereon adapted for non-slip engagement by a tool for driving the shank body into bone. Furthermore, the tool engagement formation may project from the capture structure at a tool seating surface.

Each retainer structure part or piece is sized and shaped to load into the head through either the open channel or the base opening of the head. The shank capture structure can also be sized and shape to be loadable into the head through the base opening and/or through the open channel.

An assembly according to the invention further includes a closure structure insertable into the head for operably urging the shank in a direction to frictionally lock the position of the retainer structure outer surface relative to the head seating surface, thereby locking the shank body in a selected angle with respect to the head. Furthermore, the head may include upstanding spaced arms defining the open channel, the arms having guide and advancement structures on an inside surface thereof, with the closure structure being sized and shaped to be positionable between the arms for closing the channel. The closure structure has a closure guide and advancement structure for rotatably mating with the guide and advancement structures on the arms. Upon advancing rotation between the arms, the closure structure biases against a rod disposed in the channel.

In a method according to the invention, retainer structure pieces are inserted into a polyaxial bone screw head cavity through either an upper rod-receiving channel or a lower shank receiving opening. A capture structure of a bone screw shank is then inserted into the head through the shank receiving opening of the head and into the cavity thereof. The capture structure is then moved toward the upper rod-receiving channel and the retainer structure pieces pivot about an edge of the capture structure while being moved toward the lower shank receiving opening until an inner surface of each of the retainer structure pieces is in frictional engagement with an oblique surface of the capture structure.

Furthermore, according to a method of the invention, if the retainer structure is of two-part or piece construction, the method includes simultaneously pivoting both retainer pieces about the capture structure edge and then into position about an oblique surface or surfaces of the capture structure.

It is foreseen that the retainer structure parts can be different in size and/or shape. It is foreseen that the capture structure can be cylindrical in shape with at least one inward groove or outward ridge for mating with the retainer structure. It is also foreseen that the capture structure can be spherical or elliptical in shape, with outer concave or convex surfaces, or have square upper and lower cross-sectional ends of same or different size.

Objects and Advantages of the Invention

Therefore, it is an object of the present invention to overcome one or more of the problems with polyaxial bone screw assemblies described above. A further object of the invention is to provide apparatus and methods directed to a shank that is loadable into a cavity in a head of the screw and that utilizes a retainer structure that may be uploaded or downloaded into the cavity. Another object of the invention is to provide more than one retainer parts or segments configured to be engageable with the shank and slidably engageable with the head so as to articulate or fix the head relative to the shank once a desired configuration is acquired. Furthermore, it is an object of the invention to provide a lightweight, low profile polyaxial bone screw that assembles in such a manner that the components cooperate to create an overall structure that provides an even gripping of a shank capture structure to the head, avoiding excessive local pressure therebetween. Another object of the invention is to provide such components that do not require overly complicated fasteners or complicated methods of fastening within the bone screw head. Another object of the invention is to provide a polyaxial bone screw with features that present frictional or gripping surfaces for bone implantation tools and may be readily and securely fastened to each other as well as to the bone.

Furthermore, it is an object of the invention to provide apparatus and methods that are easy to use and especially adapted for the intended use thereof and wherein the tools are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of a polyaxial bone screw assembly according to the present invention having a shank with a capture structure at one end thereof, a head, and a two-piece retainer structure.

FIG. 2 is an enlarged top plan view of the retainer structure of FIG. 1.

FIG. 3 is an enlarged cross-sectional view of the retainer structure of FIG. 2, taken along the line 3-3 of FIG. 2.

FIG. 4 is an enlarged top plan view of the shank of FIG. 1.

FIG. 7 is an enlarged cross-sectional view of the head, taken along the line 5-5 of FIG. 1, an enlarged and partial cross-sectional view of the shank, taken along the line 7-7 of FIG. 1, and shown with the retainer structure of FIG. 3 in an early assembly step according to the invention.

FIG. 8 is an enlarged and fragmentary cross-sectional view of the head, shank and retainer structure, similar to FIG. 7, showing an intermediate assembly step.

FIG. 11 is a cross-sectional view of a vertebra, and the assembled head and shank, similar to FIG. 10, showing the shank being implanted into the vertebra using a driving tool mounted on the shank capture structure.

FIG. 12 is an enlarged, front plan view of the implanted head and shank of FIG. 11, shown in exploded view with a rod (in cross-section), break-off closure structure, and closure structure driving tool.

FIG. 14 is a fragmentary front elevational view of a bone screw with attached break-away closure member, installed rod, and an anti-torque tool mounted on the rod with portions broken away to show a torque driver advancing toward the break-away closure member.

FIG. 15 is a fragmentary front elevational view similar to FIG. 14, with portions broken away to show a fully installed rod and closure member with the break-away head removed by the torque driver.

FIG. 16 is a fragmentary and enlarged perspective view of the assembly of FIG. 12 shown completely assembled.

FIG. 17 is an exploded perspective view of an alternative embodiment of a polyaxial bone screw assembly according to the present invention having a shank with an upper capture structure, a head, and a jointed two-part retainer structure.

FIG. 18 is an enlarged top plan view of the retainer structure of FIG. 17 shown in a compressed, loading orientation.

FIG. 19 is an enlarged front elevational view of the retainer structure of FIG. 18 in a compressed, loading orientation.

FIG. 20 is an enlarged front elevational view of the retainer structure of FIG. 18 shown in an expanded configuration.

FIG. 21 is an enlarged top plan view of the retainer structure of FIG. 18 shown in an expanded configuration.

FIG. 22 is an enlarged top plan view of the shank of FIG. 17.

FIG. 23 is an enlarged cross-sectional view of the head, taken along the line 23-23 of FIG. 17, shown with the compressed retainer structure of FIGS. 18 and 19 (in side-elevational view) and illustrating a method of inserting the retainer structure into the head.

FIG. 24 is an enlarged cross-sectional view of the head, taken along the line 23-23 of FIG. 17, shown with the compressed retainer structure of FIGS. 18 and 19 fully inserted in the head.

FIG. 25 is an enlarged cross-sectional view of the head, taken along the line 23-23 of FIG. 17, an enlarged and partial cross-sectional view of the shank, taken along the line 25-25 of FIG. 17, and shown with the expanded retainer structure of FIGS. 20 and 21, shown in cross-section and in an early assembly step according to the invention.

FIG. 26 is an enlarged and fragmentary cross-sectional view of the head, shank and retainer structure, similar to FIG. 25, showing an intermediate assembly step.

FIG. 27 is an enlarged and fragmentary cross-sectional view of the head, shank and retainer structure, similar to FIG. 25, showing a subsequent assembly step.

FIG. 28 is an enlarged and fragmentary cross-sectional view of the head, shank and retainer structure, similar to FIG. 25 showing a final assembly step.

FIG. 29 is an exploded perspective view of another alternative embodiment of a polyaxial bone screw assembly according to the present invention having a shank with an upper capture structure, a head, and a two-piece retainer structure.

FIG. 30 is an enlarged top plan view of the retainer structure of FIG. 29.

FIG. 31 is an enlarged cross-sectional view of the retainer structure taken along the line 31-31 of FIG. 30.

FIG. 32 is an enlarged top plan view of the shank of FIG. 29.

FIG. 35 is an enlarged cross-sectional view of the head, shank and retainer structure pieces, similar to FIG. 34, showing an intermediate assembly step according to the invention.

FIG. 36 is an enlarged and fragmentary cross-sectional view of the head, shank and retainer structure, similar to FIG. 35 showing a final assembly step.

DETAILED DESCRIPTION OF THE INVENTION

Figure 5:
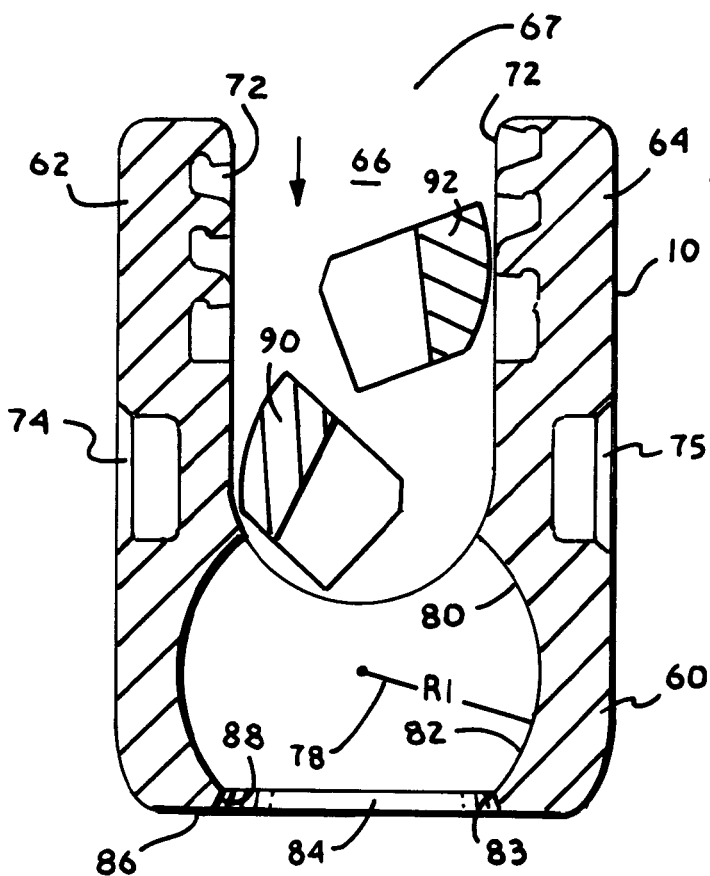
FIG. 5 is an enlarged cross-sectional view of the head, taken along the line 5-5 of FIG. 1 and shown with the retainer structure of FIG. 3 in a method of assembly according to the invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

In FIGS. 1-16 the reference number 1 generally represents a first embodiment of a polyaxial bone screw apparatus or assembly according to the present invention. The assembly 1 includes a shank, generally 4, that further includes a body 6 integral with an upwardly extending capture structure 8; a head 10; and a two-piece or part retainer structure 12. The shank 4, head 10 and retainer structure 12 preferably are assembled prior to implantation of the shank body 6 into a vertebra 15, which procedure is shown in FIG. 11.

FIG. 12 further shows a closure structure 18 of the invention for biasing a longitudinal member such as a rod 21 against the capture structure 8 which biases the retainer structure 12 into fixed frictional contact with the capture structure 8 and the head 10, so as to fix the rod 21 relative to the vertebra 15. The head 10 and the shank 4 cooperate in such a manner that the head 10 and the shank 4 can be secured at any of a plurality of angles, articulations or rotational alignments relative to one another and within a selected range of angles both from side to side and from front to rear, to enable flexible or articulated engagement of the head 10 with the shank 4 until both are locked or fixed relative to each other near the end of an implantation procedure.

The shank 4, best illustrated in FIGS. 1, 4 and 7, is elongate, with the shank body 6 having a helically wound bone implantable thread 24 extending from near a neck 26 located adjacent to the capture structure 8, to a tip 28 of the body 6 and extending radially outwardly therefrom. During use, the body 6 utilizing the thread 24 for gripping and advancement is implanted into the vertebra 15 leading with the tip 28 and driven down into the vertebra 15 with an installation or driving tool 31, so as to be implanted in the vertebra 15 to near the neck 26, as shown in FIG. 11, and as is described more fully in the paragraphs below. The shank 4 has an elongate axis of rotation generally identified by the reference letter A. It is noted that any reference to the words top, bottom, up and down, and the like, in this application refers to the alignment shown in the various drawings, as well as the normal connotations applied to such devices, and is not intended to restrict positioning of the assembly 1 in actual use.

The neck 26 extends axially outward and upward from the shank body 6. The neck 26 preferably is of slightly reduced radius as compared to an adjacent upper end or top 32 of the body 6 where the thread 24 terminates. Further extending axially and outwardly from the neck 26 is the capture structure 8 that provides a connective or capture apparatus disposed at a distance from the upper end 32 and thus at a distance from the vertebra 15 when the body 6 is implanted in the vertebra 15.

The capture structure 8 is configured for connecting the shank 4 to the head 10 and capturing the shank 4 in the head 10. The structure 8 is a polyhedral formation, specifically a polyhedron-like structure, generally 38, with front and rear parallel surfaces 40 and 41. Each of the surfaces 40 an 41 is in the shape of an inverted isosceles trapezoid. The surfaces 40 and 41 are congruent and are also parallel to the axis A. The surfaces 40 and 41 are adjacent to a top surface 44 of the structure 38, the top surface 44 being substantially planar and disposed perpendicular to the axis A. The surfaces 40 and 41 extend to an annular seating surface or ledge 45, the ledge 45 being a substantially flat surface projecting radially from the axis A and disposed parallel to the top surface 44. The top surface 44 has a width W that is greater than an outer diameter of the seating surface 45 and includes top edges 46 and 47 extending between the trapezoidal front and rear surfaces 40 and 41. Finishing out the polyhedron-like structure 38 are oblique side surfaces or faces 48 and 49, each of which are substantially rectangular in shape and slope inwardly from the top edges 46 and 47 respectively, to bottom edges 50 and 51 disposed adjacent to the annular seating surface 45. The term oblique is used herein to describe the surfaces 48 and 49 that are slanted or inclined in direction or course or position neither parallel nor perpendicular nor right-angular, with respect to the shank body 6, but otherwise may be disposed at a variety of angles with respect to the Axis A. The oblique surfaces 48 and 49 slope from the top surface 44 toward the Axis A in a direction toward the tip 28 of the shank body 6. A width W2 between the bottom edges 50 and 51 is smaller than the width W and also smaller than the outer diameter of the seating surface 45.

The shank 4 further includes a tool engagement structure 52 projecting axially from the top surface 44 to an end surface 53. The tool engagement structure 52 functions to engage the driving tool 31 shown in FIG. 11. The tool 31 includes a driving structure in the form of a socket. The tool 31 is configured to fit about the tool engagement structure 52 so as to form a socket and mating projection for both driving and rotating the shank body 6 into the vertebra 15. Specifically in the embodiment shown in FIGS. 1-16, the tool engagement structure 52 is in the shape of a hexagonally shaped extension head coaxial with the threaded shank body 6, however, other shaped extensions for tool engagement are possible, such as grooved, multi-lobular, etc.

The end surface 53 of the shank 4 is preferably curved or dome-shaped as shown in the drawings, for positive engagement with the rod 21, when the bone screw assembly 1 is assembled, as shown in FIG. 15 and in any alignment of the shank 4 relative to the head 10. In certain embodiments, the surface 53 is smooth. While not required in accordance with practice of the invention, the surface 53 may be scored or knurled to further increase frictional engagement between the surface 53 and the rod 21.

The shank 4 shown in the drawings is cannulated, having a small central bore 54 extending an entire length of the shank 4 along the axis A. The bore 54 has a first circular opening 56 at the shank tip 28 and a second circular opening 58 at the domed surface 53. The bore 54 is coaxial with the threaded body 6. The bore 54 provides a passage through the shank 4 interior for a length of wire (not shown) inserted into the vertebra 15 prior to the insertion of the shank body 6, the wire providing a guide for insertion of the shank body 6 into the vertebra 15.

With reference to FIGS. 1 and 5, the head 10 has a generally U-shaped appearance with a partially cylindrical inner profile and a substantially cylindrical outer profile. The head 10 includes a substantially cylindrical base portion 60 integral with a pair of upstanding arms 62 and 64 forming a U-shaped cradle and defining a U-shaped channel 66 between the arms 62 and 64 with an upper opening 67 and a lower seat 68 having substantially the same radius as the rod 21 for operably snugly receiving the rod 21.

Each of the arms 62 and 64 has an interior surface 70 that defines the inner cylindrical profile and includes a partial helically wound guide and advancement structure 72. In the illustrated embodiment, the guide and advancement structure 72 is a partial helically wound flangeform configured to mate under rotation with a similar structure on the closure structure 18, as described more fully below. However, it is foreseen that the guide and advancement structure 72 could alternatively be a V-shaped thread, a buttress thread, a reverse angle thread or other thread like or non-thread like helically wound advancement structures for operably guiding under rotation and advancing the closure top downward between the arms 62 and 64.

The head 10 includes external, closed end grip bores 74 and 75 disposed on the respective arms 62 and 64 for positive engagement by a holding tool (not shown) to facilitate secure gripping of the head 10 during assembly of the head 10 with the shank 4 and retainer structure 12. Furthermore, the grip bores 74 and 75 may be utilized to hold the head 10 during the implantation of the shank body 6 into the vertebra 15. The bores 74 and 75 are centrally located on the respective arms 62 and 64. However, it is noted that the bores 74 and 75 may be configured to be of a variety of sizes and locations along outer surfaces of the arms 62 and 64.

Communicating with the U-shaped channel 66 of the head 10 is a chamber or cavity 78 substantially defined by an inner surface 80 of the base 60. The cavity 78 opens upwardly into the U-shaped channel 66. The inner surface 80 is substantially spherical, with at least a portion thereof forming a partial internal spherical seating surface 82 having a first radius R1, the surface 82 for mating with the retainer structure 12, as described more fully below.

The base 60 further includes a restrictive aperture, opening or neck 83, having a second radius R2 and partially defining a bore 84 communicating with the cavity 78 and a bottom exterior 86 of the base 60. The bore 84 is coaxial with a rotational axis B of the head 10. A bevel 88 extends between the neck 83 and the bottom exterior 86. The neck 83 and associated bore 84 with radius R2 are sized and shaped to be smaller than a radial dimension of the retainer structure 12 (radius R1), when installed, as will be discussed further below, so as to form a restriction at the location of the neck 83 relative to the retainer structure 12, to prevent the structure 12 from passing between the cavity 78 and the bottom exterior 86 of the head 10, when fully seated in the head 10 and in operational engagement with the capture structure 8. The bevel 88 widens the angular range of the shank 4 when assembled with the head 10.

The two-part retainer structure 12 is used to retain the capture structure 8 of the shank 4 within the head 10 and articulate the shank body 6 with respect to the head 10. The retainer structure 12, best illustrated by FIGS. 1-3, has an operational central axis that is the same as the elongate axis A associated with the shank 4. The structure 12 includes a first piece or part 90 and a mirror image second piece or part 92. The parts 90 and 92 provide a collar or collet about the capture structure 8 within the head 10, when installed as will be discussed more fully below.

The parts or pieces 90 and 92 slidably and closely grip both the capture structure 8 and the seating surface 82, providing an even and uniform gripping surface between the shank 4 and the head 10 at the spherical seating surface 82 when force is directed onto the shank domed surface 53 by the rod 21 and closure structure 18, or by other types of longitudinal members and closure structures.

Although a two-piece retainer structure 12 is illustrated herein, it is foreseen that the retainer structure may be made up of a plurality of pieces, each slidably frictionally matable with both the capture structure 8 and the seating surface 82 of the head 10. The pieces may also be of varying sizes and not necessarily mirror images of one another. Furthermore, although the illustrated embodiment shows the parts 90 and 92 in contact with each other when fully installed in the head 10 and in contact with the shank capture structure 8, it is foreseen that the parts 90 and 92 may be sized and shaped so as to be in spaced relation to one another when fully installed with the capture structure 8 in the head 10.

Figure 10:
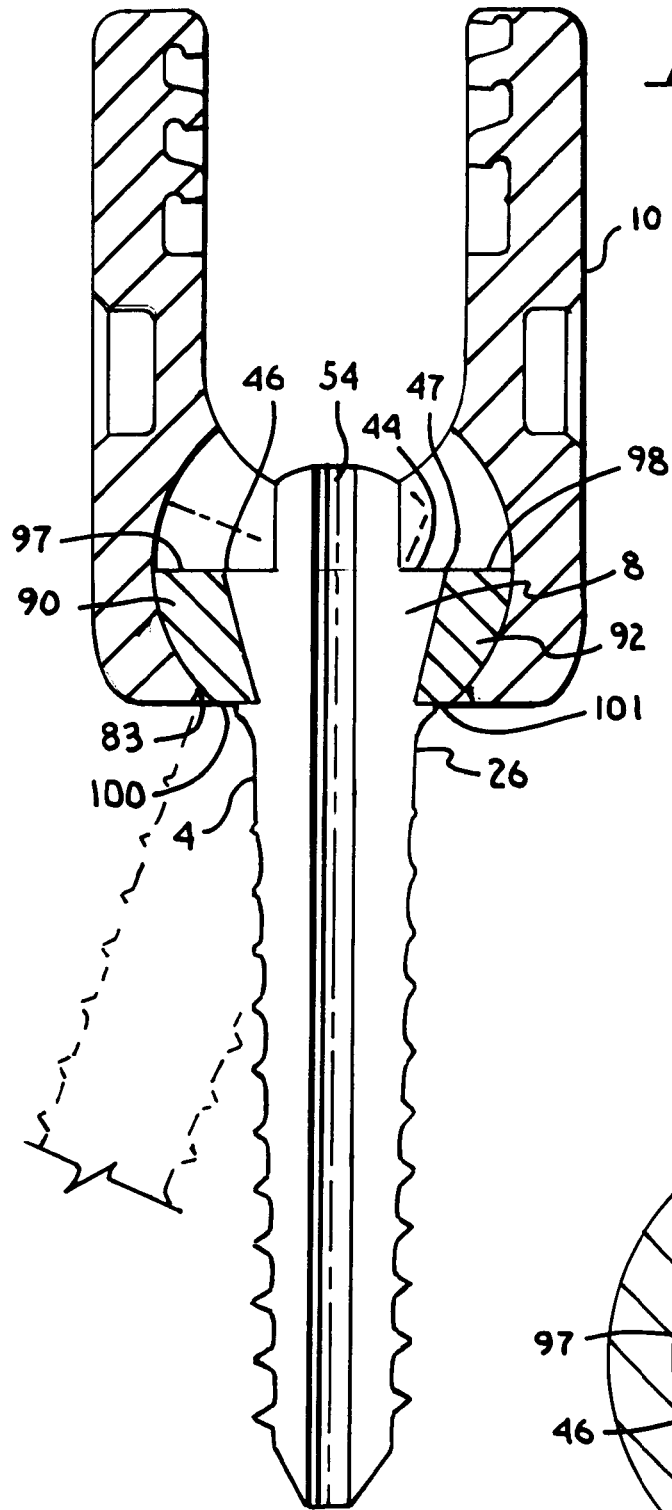
FIG. 10 is an enlarged and fragmentary cross-sectional view of the head, shank and retainer structure, similar to FIG. 9 showing a final assembly step and further showing a rotational extent of the shank in phantom.

Each retainer part 90 and 92 includes a substantially spherical outer surface, 94 and 95, respectively, each having a radius substantially corresponding to the radius R1 of the head seating surface 82. The parts 90 and 92 further include respective planar top surfaces 97 and 98 and respective planar bottom surfaces 100 and 101. The surface 97 and the surface 100 are parallel. The surface 98 and the surface 101 are parallel. The surfaces 100 and 101 abut and seat upon the annular seating surface 45 of the shank 4 when fully installed in the head 10 as shown in FIG. 10, with the top surfaces 97 and 98 disposed parallel to and substantially flush with the surface 44 of the capture structure 8.

With particular reference to FIG. 2, each of the retainer structure parts 90 and 92 have a squared-off U-shape or C-shape, when viewed from the top or bottom, formed about voids or through passages 103 and 104, respectively, from respective top surfaces 97 and 98 to respective bottom surfaces 100 and 101. The respective passages 103 and 104 are defined in part by angled or sloping surfaces 106 and 107, respectively. The surface 106 has a top edge 110 and a bottom edge 111. The surface 107 has a top edge 112 and a bottom edge 113. When the retainer structure parts 90 and 92 are operationally disposed in the head 10 with the substantially spherical surfaces 94 and 95 in frictional contact with the spherical seating surface 82, and the bottom surfaces 100 and 101 are seated on the annular seating surface 45 of the shank 4, the surfaces 106 and 107 are disposed at a degree of inclination with respect to the bottom surfaces 100 and 101, respectively, corresponding or congruent to a degree of inclination of the side surfaces 48 and 49 of the capture structure 8 with respect to the seating surface 45, such that substantially full frictional contact is made between the surface 106 and the surface 48; and substantially full frictional contact is made between the surface 107 and the surface 49.

The retainer structure part 90 further includes parallel inner walls 116 and 117, disposed perpendicular to the top and bottom surfaces 97 and 100, respectively. The retainer structure part 92 includes parallel inner walls 119 and 120, disposed perpendicular to the top and bottom surfaces 98 and 101, respectively. The walls 116 and 119 are configured to frictionally mate with the rear trapezoidal surface 41 of the capture structure 8 when the sloped surface 106 is in contact with the side surface 48; and the walls 117 and 120 are configured to frictionally mate with the front trapezoidal surface 40 of the capture structure 8 when the sloped surface 107 is in contact with the side surface 49.

It is noted that because the parts 90 and 92 are mirror images of each other, the retainer structure functions equally well with the sloped surface 106 in contact with the side surface 49 and the sloped surface 107 in contact with the side surface 48, with the respective alternative matching of the walls 116 and 119 with the front surface 40 and the walls 117 and 120 with the rear surface 41. Although the illustrated wall surfaces 106, 107, 116, 117, 119, and 120 are smooth and planar, it is foreseen that these surfaces may be roughened or abraded to provide enhanced frictional contact with the capture structure 8. Additionally or alternatively the surfaces 40, 41, 48 and 49 of the capture structure 8 may be roughened or in some way abraded to provide enhanced frictional contact with the retainer structure 12. Furthermore, the outer surfaces 94 and 95 of the retainer structure 12 that contact the substantially spherical seating surface 82 of the head may also be a high friction surface, such as a knurled surface.

Figure 13:
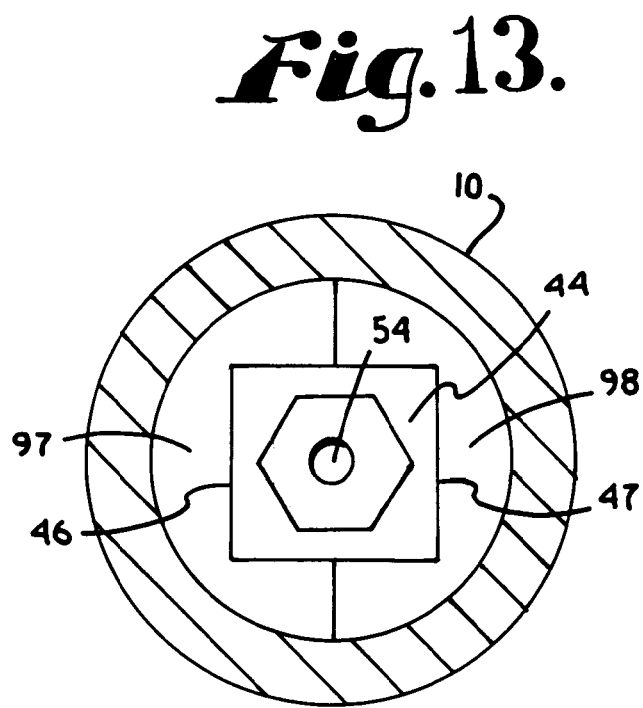
FIG. 13 is an enlarged cross-sectional view taken along the line 13-13 of FIG. 10.

The retainer part or piece 90 further includes end walls 122 and 123, extending from the outer surface 94 to the inner walls 116 and 117, respectively. The end walls 122 and 123 are disposed substantially perpendicular to the top surface 97. The wall 122 includes a top bevel 126 and the wall 123 includes a top bevel 127. The retainer part 92 further includes end walls 130 and 131, extending from the outer surface 95 to the inner walls 119 and 120, respectively. The end walls 130 and 131 are disposed substantially perpendicular to the top surface 98. The wall 130 includes a top bevel 134 and the wall 131 includes a top bevel 135. The retainer parts 90 and 92 are configured such that, when operationally disposed in the head 10, with the substantially spherical surfaces 94 and 95 in sliding frictional contact with the spherical seating surface 82, and with the bottom surfaces 100 and 101 seated on the annular seating surface 45 of the shank 4, the end walls 122 and 123 are in contact with the respective end walls 130 and 131, as illustrated in FIG. 13. The bevels 126, 127, 134, and 135 provide clearance space for installing the retainer structure parts 90 and 92 about the capture structure 8 within the head 10 in a method of the invention described subsequently herein. It is foreseen that also in accordance with the invention, to provide additional clearance during installation, the parts 90 and 92 may be configured such that the end walls 122 and 123 are in spaced, substantially parallel relation with the respective end walls 130 and 131, when fully installed in the bone screw head 10.

The elongate rod or longitudinal connecting member 21 that is utilized with the assembly 1 can be any of a variety of implants utilized in reconstructive spinal surgery, but is normally a cylindrical, elongate structure having a substantially smooth, cylindrical surface 136 of uniform diameter. The rod 21 is preferably sized and shaped to snugly seat near the bottom of the U-shaped channel 66 of the head 10 and, during normal operation, is positioned slightly above the bottom of the channel 66 at the lower seat 68. In particular, the rod 21 normally directly or abutingly engages the shank top end surface 53, as shown in FIG. 12 and is biased against the domed surface 53, consequently biasing the shank 4 downwardly in a direction toward the base 60 of the head 10 when the assembly 1 is fully assembled. For this to occur, the shank top end surface 53 must extend at least slightly into the space of the channel 66 when the retainer structure 12 is snugly seated on the shank 4 in the lower part of the head cavity 78. The shank 4 and retainer structure 12 are thereby locked or held in position relative to the head 10 by the rod 21 firmly pushing downward on the shank top end surface 53. It is foreseen, however, that in other embodiments according to the invention, a top- or side-loadable insert may be positioned between the rod 21 and the top end surface 53 and cooperating pieces 90 and 92, the insert initially engageable with the top surface 53 and one or both pieces 90 and 92. In such an embodiment, it would not be necessary for the shank top end surface 53 to extend into the space of the channel 66. Such an insert may be positioned in the bone screw head utilizing a variety of mechanisms, such as a ratchet or twist-and-lock system, and may be used to set the bone screw shank into position with respect to the head prior to insertion of the rod. After placement of the rod in the bone screw head, the insert would engage both the rod and the top surface 53 to secure the bone screw shank in a desired position.

With reference to FIGS. 12 and 14-16, the closure structure or closure top 18 can be any of a variety of different types of closure structures for use in conjunction with the present invention with suitable mating structure on the upstanding arms 62 and 64. The closure top 18 screws between the spaced arms 62 and 64.

The illustrated closure top 18 has a generally cylindrical shaped base 138 with a lower point or projection 139 for abrading or digging into the rod 21, and an upwardly extending break-off head 140. The base 138 includes a helically wound guide and advancement structure 141 that is sized, shaped and positioned so as to engage the guide and advancement structure 72 on the arms 62 and 64 to provide for rotating advancement of the closure structure 18 into the head 10 when rotated clockwise and, in particular, to cover the top or upwardly open portion 67 of the U-shaped channel 66 to capture the rod 21, preferably without splaying of the arms 62 and 64. The closure structure 18 also operably biases against the rod 21 by advancement and applies pressure to the rod 21 under torquing, so that the rod 21 is urged downwardly against the shank top end surface 53 that extends into the channel 66. Downward biasing of the shank top surface 53 operably produces a frictional engagement between the rod 21 and the surface 53 and also urges the retainer structure 12 toward the base 60 of the head 10, so as to frictionally seat the retainer structure 12 external spherical surfaces 94 and 95 fixedly against the partial internal spherical seating surface 82 of the head 10, also fixing the shank 4 and retainer structure 12 in a selected, rigid position relative to the head 10.

The closure structure break-off head 140 is secured to the base 138 at a neck 144 that is sized and shaped so as to break away at a preselected torque that is designed to properly seat the retainer structure 12 in the head 10. The break-off head 140 includes a central bore 145 and grooves 146 for operably receiving a driving and manipulating tool 147 having a projection 148 receivable in the bore 145 and stops 149 receivable in the grooves 146. The break-off head 140 further includes an external faceted surface 150, sized and shaped to receive a conventional mating socket type head of a torquing tool 152 to rotate and torque the closure structure 18. An anti-torque tool 153 may also be provided as shown in FIGS. 14 and 16 that extends about the head 10 and engages the rod 21 to hold the apparatus 1 stationary during rotation of the torquing tool 152.

The closure structure 18 also includes removal tool engagement structure which in the present embodiment is in the form of a hex-shaped and axially aligned aperture 154 disposed in the base 138, as shown in FIG. 16. The hex aperture 154 is accessible after the break-off head 140 breaks away from the base 138. The aperture 154 is coaxial with the helically wound guide and advancement structure 141 and is designed to receive a hex tool, of an Allen wrench type, into the aperture 154 for rotating the closure structure base 138 subsequent to installation so as to provide for removal thereof, if necessary. Although a hex-shaped aperture 154 is shown in the drawings, the tool engagement structure may take a variety of tool-engaging forms and may include more than one aperture of various shapes, such as a pair of spaced apertures, a left hand threaded bore, an easyout engageable step down bore or the like.

Figure 6:
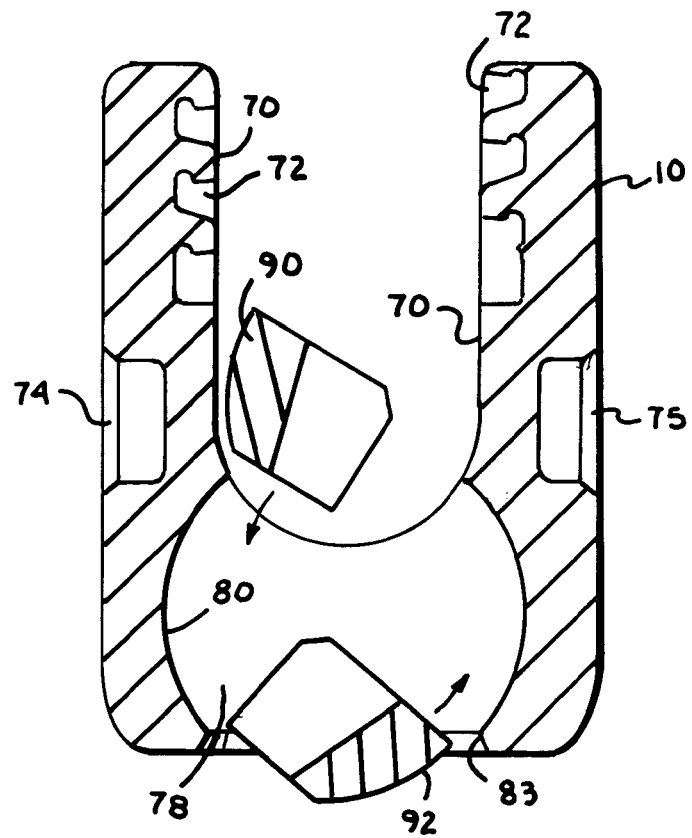
FIG. 6 is an enlarged cross-sectional view of the head, taken along the line 5-5 of FIG. 1, and shown with the retainer structure of FIG. 3 in an alternative method of assembly according to the invention.

Prior to the polyaxial bone screw assembly 1 being placed in use according to the invention, the retainer structure pieces 90 and 92 are typically first inserted or top-loaded into the head U-shaped channel 66, as shown in FIG. 5, and then into the cavity 78 to dispose the structure 12 adjacent to the inner surface 80 of the head 10. Alternatively, as shown in FIG. 6, one of the retainer structure pieces 90 is inserted or top-loaded into the channel 66, while the other retainer structure piece 92, is inserted or bottom-loaded into the cavity 78 through the bore 84. Alternatively, both pieces 90 and 92 may be uploaded through the bore 84 (not shown).

Figure 9:
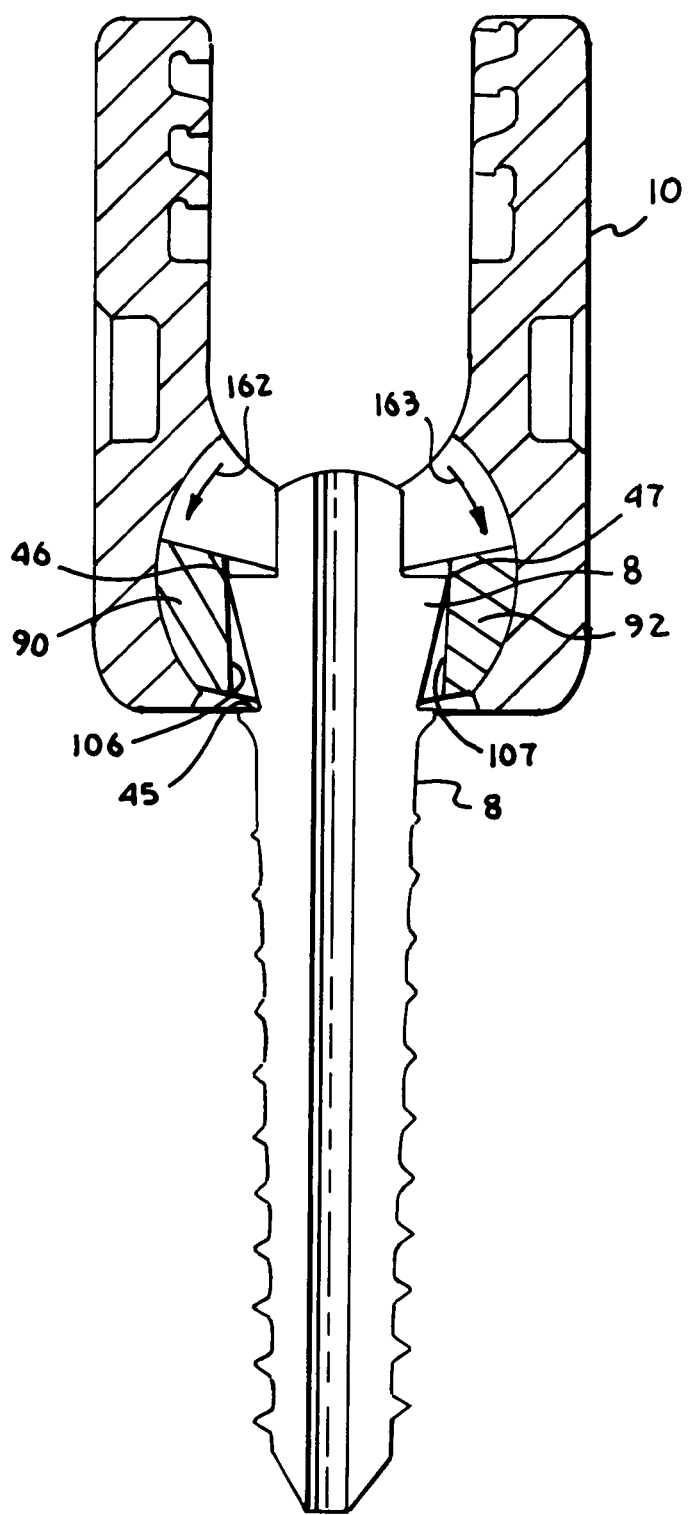
FIG. 9 is an enlarged and fragmentary cross-sectional view of the head, shank and retainer structure, similar to FIG. 8, showing a subsequent assembly step.

With reference to FIG. 7, after the retainer pieces 90 and 92 are disposed in the cavity 78, the shank 4 is inserted or up-loaded into the head 10 through the bore 84 as indicated by an arrow 160. With reference to FIG. 8, the top edges 46 and 47 of the trapezoidal capture structure 8 come into contact with the sloping inner surfaces 106 and 107 of the respective retainer pieces 90 and 92. Initially all three components, the capture structure 8, and the pieces 90 and 92 may move upwardly as illustrated by the arrow 160 in FIG. 8. With reference to FIG. 9, as the capture structure 8 continues to move upwardly and into the cavity 78 as shown by the arrow 160, the retainer structure pieces 90 and 92 pivot about the edges 46 and 47 and begin to move downwardly toward the base 60 as shown by the arrows 162 and 163.

With reference to FIG. 10, the pieces 90 and 92 continue the downward movement until the bottom surfaces 100 and 101 abut and seat upon the annular seating surface 45 of the shank 4. Once seated upon the annular surface 45, the retainer structure sloping surface 106 frictionally engages the capture structure side surface 48 and the sloping retainer structure surface 107 frictionally engages the capture structure side surface 49.

Subsequent slight downward movement by the shank 4, as well as the frictionally engaged retainer pieces 90 and 92, shown by the arrow 166 in FIG. 10, seats the shank/retainer structure assembly in the head cavity 78, with the retainer surfaces 94 and 95 in sliding engagement with the head seating surface 82. The retainer structure 12, now fully seated in the head 10 is coaxially aligned with the shank capture structure 8. With reference to the shank 6 shown in phantom in FIG. 10, at this time, the capture structure 8, the retainer structure 12, the head seating surface 82 and the lower aperture or neck 83 cooperate to maintain the shank body 6 in rotational relation with the head 10. According to the embodiment of the invention shown in FIGS. 1-16, only the retainer structure 12 is in slidable engagement with the head spherical seating surface 82. Both the capture structure 8 and the threaded portion of the shank body 6 are in spaced relation with the head 10. An extent of rotation is shown in FIG. 10 where it is illustrated that the shank body 6 can be rotated through a substantial angular rotation relative to the head 10, both from side to side and from front to rear so as to substantially provide a universal or ball joint wherein the angle of rotation is only restricted by engagement of the neck 26 of the shank body 6 with the restrictive neck 83 of the head 10.

With reference to FIG. 11, the assembly 1 is then typically screwed into a bone, such as the vertebra 15, by rotation of the shank 4 using the driving tool 31 that operably drives and rotates the shank 4 by engagement thereof with the hexagonally shaped extension or tool engagement head 52 of the shank 4. Preferably, when the driving tool 31 engages the head 52, an end portion thereof abuts and frictionally engages the top surface 44 of the capture structure 8.

Typically, the head 10 and the retainer structure 12 are assembled on the shank 4 before implanting the shank body 6 into the vertebra 15. Also, the vertebra 15 may be pre-drilled to minimize stressing the bone and have a guide wire (not shown) inserted therein to provide a guide for the placement and angle of the shank 4 with respect to the vertebra 15. A further tap hole may be made using a tap with the guide wire as a guide. Then, the assembly 1 is threaded onto the guide wire by first threading the wire into the bottom opening 56 and then out of the top opening 58 of the cannulation bore 54. The shank 4 is then driven into the vertebra 15, using the wire as a placement guide.

With reference to FIGS. 12 and 14-16, the rod 21 is eventually positioned within the head U-shaped channel 66, and the closure structure or top 18 is then inserted into and advanced between the arms 62 and 64 with the driving and manipulation tool 147 so as to bias or push against the rod 21. The anti-torque tool 153 is then placed in position about the head 10 and the rod 21 as shown in FIGS. 13 and 14, and the torquing tool or driver 152 is inserted about the break-off head 140. The break-off head 140 is then twisted to a preselected torque utilizing the torque driver 152, for example 90 to 120 inch pounds, to urge the rod 21 downwardly into a final desired position.

The shank top end surface 53, because it is rounded to approximately equally extend upward into the channel 66 approximately the same amount no matter what degree of rotation exists between the shank 4 and head 10 and because the surface 53 is sized to extend upwardly into the U-shaped channel 66, the surface 53 is engaged by the rod 21 and pushed downwardly toward the base portion 60 of the head 10 when the closure structure 18 biases downwardly toward and onto the rod 21. The downward pressure on the shank 4 in turn urges the retainer structure 12 pieces 90 and 92 downward and radially outward, toward the head seating surface 82, with the retainer structure outer substantially spherical surfaces 94 and 95 in frictional engagement with the head seating surface 82. The radially outward forces placed upon the pieces 90 and 92 by the capture structure inverted inclined side surfaces 48 and 49 also function to retain the pieces 90 and 92 within the head cavity 78. As the closure structure 18 presses against the rod 21, the rod 21 presses against the integral capture structure 8 and shank body 6, and also the retainer structure 12 pieces 90 and 92 that are now frictionally engaged with the capture structure 8 and disposed or sandwiched between the capture structure trapezoidal structure 38 and the head 10. Because of the location and configuration of the retainer structure pieces 90 and 92, the shank 4 in turn becomes frictionally and rigidly attached to the head 10, fixing the shank body 6 in a desired angular configuration with respect to the head 10 and the rod 21.

FIG. 16 illustrates the polyaxial bone screw assembly 1 and including the rod 21 and the closure structure 18. The axis A of the bone shank 4 is illustrated as not being coaxial with the axis B of the head 10 and the shank 4 is fixed in this angular locked configuration. Other angular configurations can be achieved, as required during installation surgery due to positioning of the rod 21 or the like.

If removal of the assembly 1 and associated rod 21 and closure structure 18 is necessary, disassembly is accomplished by using a driving tool of an Allen wrench type (not shown) mating with the aperture 154 and rotating the wrench counterclockwise to rotate the base 138 and reverse the advancement thereof in the head 10. Then, disassembly of the assembly 1 is accomplished in reverse order to the procedure described previously herein for assembly.

With reference to FIGS. 17-28, the reference number 201 generally represents a second or alternative embodiment of a polyaxial bone screw apparatus or assembly according to the present invention. The assembly 201 includes a jointed, telescoping, two-part or piece retainer structure 212. The assembly 201 further includes the shank 4 and the head 10 according to the first embodiment of the apparatus according to the invention, described previously herein. Therefore, all of the reference numbers already identified herein with respect to the shank 4 and the head 10 are incorporated into the drawing FIGS. 17-26 and the description thereof are incorporated by reference herein with respect to the assembly 201.

As with the first embodiment previously described herein, the shank 4, head 10 and the retainer structure 212 preferably are assembled prior to implantation of the shank body 6 into the vertebra 15, the procedure of which has been previously described herein as shown in FIG. 11.

Furthermore, the closure structure 18 shown in FIGS. 12 and 14-16, as well as the rod 21, and optionally an insert disposed below the rod, may be utilized with the assembly 201, with the same functions and benefits, also as previously described herein.

The two-part, jointed, slidably telescoping and detachable retainer structure 212 is used to retain the capture structure 8 of the shank 4 within the head 10 and articulate the shank body 6 with respect to the head 10. The retainer structure 212, best illustrated by FIGS. 17-21, has an operational central axis that is the same as the elongate axis A associated with the shank 4. The structure 212 includes a first piece or part 220 and a substantially mirror image second piece or part 222, with the exception that the part 220 has formed therein first and second narrow recesses 224 and 225 and the part 222 includes first and second extensions 228 and 229 that cooperate with the recesses 224 and 225, respectively. The extensions 228 and 229 and cooperating recesses 224 and 225, respectively, allow for the retainer structure 212 to be telescoped inwardly or otherwise slightly collapsed into an oval-like shape to fit into the restricted space of either the channel 66 or the bore 84 of the head 10, providing for either top- or bottom-loading of the retainer structure 212 into the head 10. After the structure 212 is disposed in the cavity 78 of the head 10, the parts 220 and 222 telescope outwardly, with a portion of the extensions 228 and 229 disposed in the recesses 224 and 225, respectively, the structure 212 providing a collar or collet about the capture structure 8 and frictionally attached thereto, while also seating fully and frictionally attaching to the seating surface 82 of the head 10, when installed. As will be discussed more fully below, the parts or pieces 220 and 222 slidably and closely grip both the capture structure 8 and the seating surface 82, providing an even and uniform gripping surface between the shank 4 and the head 10 at the spherical seating surface 82 when force is directed onto the shank domed surface 53 by the rod 21 and closure structure 18, or by other types of longitudinal members and closure structures.

Each retainer part 220 and 222 includes a substantially spherical outer surface, 234 and 235, respectively, each having a radius substantially corresponding to the radius R1 of the head seating surface 82. The parts 220 and 222 further include respective planar top surfaces 237 and 238 and respective planar bottom surfaces 240 and 241. The surface 237 and the surface 240 are substantially parallel. The surface 238 and the surface 241 are substantially parallel. The surfaces 240 and 241 abut and seat upon the annular seating surface 45 of the shank 4 when fully installed in the head 10 as shown in FIG. 28, with the top surfaces 237 and 238 disposed parallel to and substantially flush with the surface 44 of the capture structure 8.

With particular reference to FIGS. 17 and 21, each of the retainer structure parts 220 and 222 have a squared-off U-shape or C-shape, when viewed from the top or bottom, formed about an open through passage 243, respectively, from the respective top surfaces 237 and 238 to the respective bottom surfaces 240 and 241. The through passage 243 is defined in part by inclined or sloping surfaces 246 and 247 disposed on parts 220 and 222, respectively. The surface 246 has a top edge 250 and a bottom edge 251. The surface 247 has a top edge 252 and a bottom edge 253. When the retainer structure parts 220 and 222 are operationally disposed in the head 10 with the substantially spherical surfaces 234 and 235 in frictional contact with the spherical seating surface 82, and the bottom surfaces 240 and 241 are seated on the annular seating surface 45 of the shank 4, the surfaces 246 and 247 are disposed at a degree of inclination with respect to the bottom surfaces 240 and 241, respectively, corresponding or congruent to a degree of inclination of the side surfaces 48 and 49 of the capture structure 8 with respect to the seating surface 45, such that substantially full frictional contact is made between the surface 246 and the surface 48; and substantially full frictional contact is made between the surface 247 and the surface 49.

The retainer structure part 220 further includes parallel inner walls 256 and 257, disposed perpendicular to the top and bottom surfaces 237 and 240. The retainer structure part 222 includes parallel inner walls 259 and 260, disposed perpendicular to the top and bottom surfaces 238 and 241. The walls 256 and 259 are configured to frictionally mate with the rear trapezoidal surface 41 of the capture structure 8 when the sloped surface 246 is in contact with the side surface 48; and the walls 257 and 260 are configured to frictionally mate with the front trapezoidal surface 40 of the capture structure 8 when the sloped surface 247 is in contact with the side surface 49.

It is noted that because the parts 220 and 222 are substantial mirror images of each other, the retainer structure functions equally well with the sloped surface 246 in contact with the side surface 49 and the sloped surface 247 in contact with the side surface 48, with the respective alternative matching of the walls 256 and 259 with the front surface 40 and the walls 257 and 260 with the rear surface 41. Although the illustrated wall surfaces 246, 247, 256, 257, 259, and 260 are smooth and planar, it is foreseen that these surfaces may be roughened or abraded to provide enhanced frictional contact with the capture structure 8. Additionally or alternatively the surfaces 40, 41, 48 and 49 of the capture structure 8 may be roughened or in some way abraded to provide enhanced frictional contact with the jointed retainer structure 212. Furthermore, the outer surfaces 234 and 235 of the retainer structure 212 that contact the substantially spherical seating surface 82 of the head may also be a high friction surface, such as a knurled surface.

The retainer part or piece 220 further includes lower end walls 262 and 263, bounded by the outer surface 234 and the inner walls 256 and 257, respectively. The end walls 262 and 263 are disposed substantially perpendicular to the top surface 237. The retainer part 222 further includes lower end walls 266 and 267, bounded by the outer surface 235 and the inner walls 259 and 260, respectively. The end walls 266 and 267 are disposed substantially perpendicular to the top surface 238.

The recesses 224 and 225 formed in the part 220 open at the end walls 262 and 263, respectively. The recesses 224 and 225 are elongate, extending substantially parallel to the top surface 237. The recesses 224 and 225 are configured to slidably receive the joint extensions 228 and 229, respectively. Furthermore, each of the recesses 224 and 225 is defined in part by an upper surface 268 and a lower surface 269. The upper surface terminates at a side or end surface 270 and the lower surface terminates at an upwardly projecting lip 271. Each of the extensions 228 and 229 is elongate and includes a knob-like protrusion 272 at an end thereof. The knob-like protrusion 272 is configured to be received in respective recesses 224 and 225 and during insertion abuts against a U-shaped surface 273 that connects the upper surface 268 with the lower surface 269. As illustrated in FIGS. 19, 20 and 25, the lower lip 271 terminates at the end walls 262 and 263, each of which extends from the lip 271 to the respective bottom 240 and 241. After the knob-like protrusions 272 are received into the recesses 224 and 225, a lower portion 274 of the protrusion 272 disposed adjacent to the extensions 228 and 229 is abutable against the lip 271, the lip 271 partially containing the protrusion 272 in position within the recesses 224 and 225. The lip 272 further functions as a pivot point for rotational movement of the retainer piece 222 with respect to the retainer piece 220 during insertion of the capture structure 8 into the head 10 as will be described more fully below, with such rotation limited by the abutment of the top surfaces of the joint extensions 228 and 229 against the upper end surface 270 of the retainer piece 220.

The recesses 224 and 255 each have a depth such that the retainer parts 220 and 222 may be slid together until the walls 262 and 266 abut, and the walls 263 and 267 abut, resulting in an oval-shaped structure 212 of a reduced width as shown in FIGS. 18 and 19, for down-loading or up-loading the structure 212 into the head 10 as will be described more fully below. Also, the retainer parts 220 and 222 are configured such that, when operationally disposed in the head 10, with the substantially spherical surfaces 234 and 235 in sliding frictional contact with the spherical seating surface 82, and with the bottom surfaces 240 and 241 seated on the annular seating surface 45 of the shank 4, the respective end walls 262 and 263 are in spaced, substantially parallel relation with the respective end walls 266 and 267 as shown in FIGS. 20 and 21, with the joint extensions 228 and 229 partially disposed within the respective recesses 224 and 225.

Prior to the polyaxial bone screw assembly 201 being placed in use according to the invention, the retainer structure pieces 220 and 222 are assembled by inserting the knob-like protrusions 272 into the recesses 224 and 225 and then sliding the protrusions 272 into the recesses 224 and 225 until the retainer piece 222 abuts against the retainer piece 220. The connected parts 220 and 222 are then inserted or top-loaded into the head U-shaped channel 66, as shown in FIG. 23, rotated such that the oblong or longest width of the structure 212 is disposed vertically as illustrated in FIG. 23. The structure 212 is then inserted into the cavity 78 by rotation as illustrated in FIG. 24, to dispose the structure 12 adjacent to the inner surface 80 of the head 10. Alternatively, the connected, abutting pieces 220 and 222 may be uploaded through the bore 84 (not shown).

With reference to FIG. 25, after the retainer structure 212 is disposed in the cavity 78, the pieces 220 and 222 are telescoped or spread apart outwardly, radially and the shank 4 is inserted or up-loaded into the head 10 through the bore 84, the direction illustrated by an arrow 275. With reference to FIG. 26, the top edges 46 and 47 of the trapezoidal capture structure 8 come into contact with the sloping inner surfaces 246 and 247 of the respective retainer pieces 220 and 222. Initially all three components, the capture structure 8, and the pieces 220 and 222 may move upwardly as illustrated by the arrow 175, causing the retainer structure 212 to rotate or hinge in the direction of arrows 278 and 279 as shown in FIG. 26. With reference to FIG. 27, as the capture structure 8 continues to move upwardly and into the cavity 78 as shown by the arrow 275, the retainer structure 212 hinges or pivots about the edges 46 and 47 and begin to move downwardly toward the base 60 as shown by the arrows 282 and 283. The hinged or jointed pieces 220 and 222 continue the downward and radial movement until the bottom surfaces 240 and 241 abut and seat upon the annular seating surface 45 of the shank 4. With reference to FIG. 28, once seated upon the annular surface 45, the retainer structure sloping surface 246 frictionally engages the capture structure side surface 48 and the sloping retainer structure surface 247 frictionally engages the capture structure side surface 49.

Subsequent slight downward movement by the shank 4, as well as the frictionally engaged retainer structure 212, may be desired to fully seat the shank/retainer structure assembly in the head cavity 78, with the retainer surfaces 234 and 235 in sliding engagement with the head seating surface 82. The retainer structure 212, now fully seated in the head 10 is coaxially aligned with the shank capture structure 8. At this time, the capture structure 8, the retainer structure 212, the head seating surface 82 and the lower aperture or neck 83 cooperate to maintain the shank body 6 in rotational relation with the head 10. According to the embodiment of the invention shown in FIGS. 17-28, only the retainer structure 212 is in slidable engagement with the head spherical seating surface 82. Both the capture structure 8 and the threaded portion of the shank body 6 are in spaced relation with the head 10. An extent of rotation similar to that shown in FIG. 10 with respect to the assembly 1 is also possible with the assembly 201 of the invention. The shank body 6 can be rotated through a substantial angular rotation relative to the head 10, both from side to side and from front to rear so as to substantially provide a universal or ball joint wherein the angle of rotation is only restricted by engagement of the neck 26 of the shank body 6 with the restrictive neck 83 of the head 10.

With reference to FIGS. 12 and 14-16 described earlier herein with respect to the assembly 1, the assembly 201 is similarly screwed into a bone, such as the vertebra 15, by rotation of the shank 4 using the driving tool 31 that operably drives and rotates the shank 4 by engagement thereof with the hexagonally shaped extension or tool engagement head 52 of the shank 4. Preferably, when the driving tool 31 engages the head 52, an end portion thereof abuts and frictionally engages the top surface 44 of the capture structure 8.

Typically, the head 10 and the retainer structure 212 are assembled on the shank 4 before implanting the shank body 6 into the vertebra 15. The steps of preparing the vertebra 15 for bone screw insertion, the bone screw implanting process, the rod reduction and closure top installment processes, and closure top removal process described herein with respect to the assembly 1 may also be performed with the assembly 201. Such processes and above-described apparatus of the assembly 1 are incorporated by reference herein with respect to the assembly 201.

With reference to FIGS. 29-36 the reference number 301 generally represents a third embodiment of a polyaxial bone screw apparatus or assembly according to the present invention. The assembly 301 includes a shank 304 that further includes a body 306 integral with an upwardly extending, substantially conical capture structure 308 and a two-piece or part retainer structure 312 configured to cooperate with the conical capture structure 308. The assembly further includes the head 10 of the first assembly 1 described previously herein. Therefore, all of the reference numbers previously identified with respect to the head 10 are incorporated into the drawing FIGS. 29-36 and the description thereof are incorporated by reference herein with respect to the assembly 301.

The shank 304, the head 10 and the retainer structure 312 preferably are assembled prior to implantation of the shank body 306 into a vertebra (not shown), but similar to the vertebra 15 shown in FIG. 11, and the procedure described herein with respect to the assembly 1 and FIG. 12. Furthermore, the closure structure 18 shown in FIGS. 12 and 14-16, as well as the rod 21 shown therein may be utilized with the assembly 301, as described with respect to the assembly 1 and incorporated by reference herein with respect to the assembly 301. It is foreseen that an insert engageable with the rod 21 may also be utilized as described herein with respect to the assembly 1. The head 10 and the shank 304 cooperate in such a manner that the head 10 and the shank 304 can be secured at any of a plurality of angles, articulations or rotational alignments relative to one another and within a selected range of angles both from side to side and from front to rear, to enable flexible or articulated engagement of the head 10 with the shank 304 until both are locked or fixed relative to each other near the end of an implantation procedure.

Figure 33:
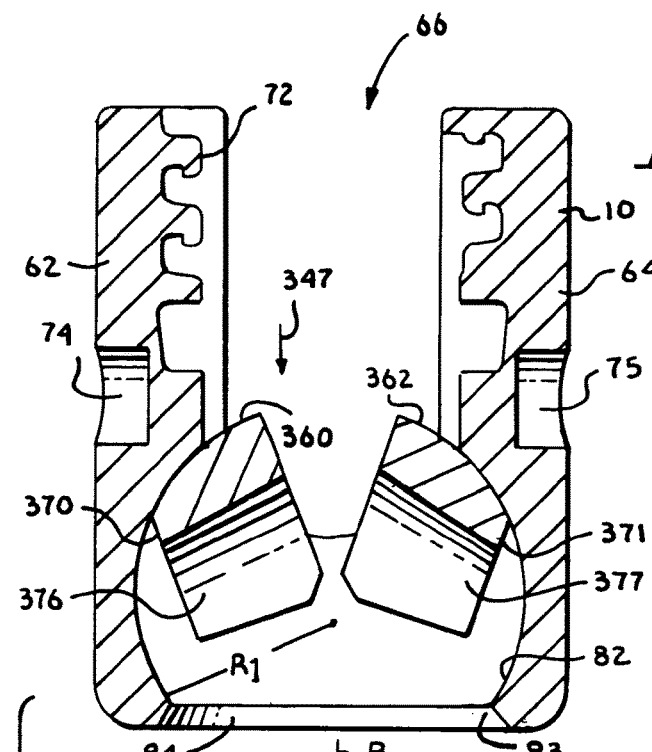
FIG. 33 is an enlarged cross-sectional view of the head and shank, taken along the line 33-33 of FIG. 29, shown with the retainer structure of FIG. 29 (also in cross-section), illustrating a method of inserting the retainer structure pieces into the head.

The shank 304, best illustrated in FIGS. 29 and 33, is elongate, with the shank body 306 having a helically wound bone implantable thread 324 extending from near a neck 326 located adjacent to the capture structure 308, to a tip 328 of the body 306 and extending radially outwardly therefrom. During use, the body 306 utilizing the thread 324 for gripping and advancement is implanted into a vertebra leading with the tip 328 and driven down into the vertebra with an installation or driving tool, such as the tool 31 shown in FIG. 11, so as to be implanted in the vertebra to near the neck 326. The shank 304 has an elongate axis of rotation generally identified by the reference letter A'.

The neck 326 extends axially outward and upward from the shank body 306. The neck 326 is of slightly reduced radius as compared to an adjacent upper end or top 332 of the body 306 where the thread 324 terminates. Further extending axially and outwardly from the neck 326 is the capture structure 308 that provides a connective or capture apparatus disposed at a distance from the upper end 332 and thus at a distance from a vertebra when the body 306 is implanted in the vertebra.

The capture structure 308 is configured for connecting the shank 304 to the head 10 and capturing the shank 304 in the head 10. The structure 308 is an inverted conical formation, with an outer conical surface or face 338. The surface 338 extends between a substantially annular top surface 344 and a substantially annular seating surface or ledge 345 disposed adjacent to the neck 326. Both the top surface 344 and the seating surface 345 are substantially planar, project radially from the axis A' and are disposed perpendicular to the axis A'. The top surface 344 has an outer circular edge 348 that is also the outer edge of the conical surface 338. The conical surface 338 has a lower, circular edge 350 that also defines an inner edge of the seating surface 345. The outer edge 348 has a diameter D1 that is greater than a diameter D2 of the inner edge 340. The diameter D1 is also larger than an outer diameter of the seating surface 345.

The shank 304 further includes a tool engagement structure 352 projecting axially from the top surface 344 to a dome-shaped end surface 353. The tool engagement structure 352 functions to engage the driving tool 31 shown in FIG. 11. The tool 31 includes a driving structure in the form of a socket. The tool 31 is configured to fit about the tool engagement structure 352 so as to form a socket and mating projection for both driving and rotating the shank body 306 into a vertebra. Specifically in the embodiment shown in FIGS. 29 and 32, the tool engagement structure 352 is in the shape of a hexagonally shaped extension head coaxial with the threaded shank body 306.

The end surface 353 of the shank 304 is preferably curved or dome-shaped as shown in the drawings, for positive engagement with the rod 21, when the bone screw assembly 301 is assembled, and in any alignment of the shank 304 relative to the head 10. In certain embodiments, the surface 353 is smooth. While not required in accordance with practice of the invention, the surface 353 may be scored or knurled to further increase frictional engagement between the surface 353 and the rod 21.

The shank 304 shown in the drawings is cannulated, having a small central bore 354 extending an entire length of the shank 304 along the axis A'. The bore 354 has a first circular opening 356 at the shank tip 328 and a second circular opening 358 at the domed surface 353. The bore 354 is coaxial with the threaded body 306. The bore 354 provides a passage through the shank 304 interior for a length of wire (not shown) inserted into a vertebra prior to the insertion of the shank body 306, the wire providing a guide for insertion of the shank body 306 into the vertebra.

The two-part or piece retainer structure 312 is used to retain the capture structure 308 of the shank 304 within the head 10 and articulate the shank body 306 with respect to the head 10. The retainer structure 312, best illustrated by FIGS. 29-31, has an operational central axis that is the same as the elongate axis A' associated with the shank 304. The structure 312 includes a discrete first piece or part 360 and a discrete mirror image second piece or part 362. The parts 360 and 362 cooperate to provide a restraining and articulating discontinuous collar or collet about the capture structure 308 within the head 10, when installed therein, as will be discussed more fully below.

The retainer parts or pieces 360 and 362 slidably and closely grip both the capture structure 308 and the seating surface 82 of the head 10, providing an even and uniform gripping surface between the shank 304 and the head 10 at the spherical seating surface 82 when force is directed onto the shank domed surface 353 by the rod 21 and closure structure 18, or by other types of longitudinal members and closure structures.

Although a two-piece retainer structure 312 is illustrated herein, it is foreseen that the retainer structure is more than one and up to a plurality of pieces, each slidably frictionally matable with both the capture structure 308 and the seating surface 82 of the head 10. The pieces may also be of varying sizes and not necessarily mirror images of one another.

Each retainer part 360 and 362 includes a substantially spherical outer surface, 364 and 365, respectively, each having a radius substantially corresponding to the radius R1 of the head seating surface 82. The parts 360 and 362 further include respective planar top surfaces 367 and 368 and respective planar bottom surfaces 370 and 371. The surface 367 and the surface 370 are substantially parallel. The surface 368 and the surface 371 are substantially parallel. The surfaces 370 and 371 abut and seat upon the annular seating surface 345 of the shank 304 when fully installed in the head 10, as shown in FIG. 32, with the top surfaces 367 and 368 disposed parallel to and substantially flush with the surface 344 of the capture structure 308.

With particular reference to FIG. 30, each of the retainer structure parts 360 and 362 have a C-shape, when viewed from the top or bottom, formed about voids or through passages 373 and 374, respectively, from respective top surfaces 367 and 368 to respective bottom surfaces 370 and 371. The respective passages 373 and 374 are defined in part by inclined or sloping, inner conical surfaces 376 and 377, respectively. The surface 376 has a semi-circular top edge 380 and a semi-circular bottom edge 381. The surface 377 has a semi-circular top edge 382 and a semi-circular bottom edge 383. When the retainer structure parts 360 and 362 are operationally disposed in the head 10 with the substantially spherical surfaces 364 and 365 in frictional contact with the spherical seating surface 82, and the bottom surfaces 370 and 371 are seated on the annular seating surface 345 of the shank 304, the inner conical surfaces 376 and 377 are disposed at a degree of inclination with respect to the bottom surfaces 370 and 371, respectively, corresponding or congruent to a degree of inclination of the conical surface 338 of the capture structure 308 with respect to the seating surface 345, such that substantially full frictional contact is made between the surface 338 and both the surfaces 376 and 377.

With reference to FIG. 31, although the inner conical surfaces 376 and 377 are shown in the drawing figures as smooth and planar, it is foreseen that these surfaces may be roughened or abraded to provide enhanced frictional contact with the capture structure 308. Additionally or alternatively the conical surface 338 of the capture structure 308 may be roughened or in some way abraded to provide enhanced frictional contact with the retainer structure 312. Furthermore, the outer surfaces 364 and 365 of the retainer structure 312 that contact the substantially spherical seating surface 82 of the head may also be a high friction surface, such as a knurled surface.

The retainer structure part 360 further includes planar end walls 386 and 387, disposed perpendicular to the top and bottom surfaces 367 and 370, respectively. The retainer structure part 362 includes planar end walls 389 and 390, disposed perpendicular to the top and bottom surfaces 368 and 371, respectively. The walls 386, 387, 389 and 390 each include a top bevel 395. The retainer parts 360 and 362 are configured such that, when operationally disposed in the head 10, with the substantially spherical surfaces 364 and 365 in sliding frictional contact with the spherical seating surface 82, and with the bottom surfaces 370 and 371 seated on the annular seating surface 345 of the shank 304, the end walls 386 and 387 are in spaced, substantially parallel relation with the respective end walls 389 and 390, but may also be in contact with one another. The bevels 395 provide clearance space for installing the retainer structure parts 360 and 362 about the capture structure 308 within the head 10 in a method of the invention described subsequently herein.

With reference to FIG. 33, prior to the polyaxial bone screw assembly 301 being placed in use according to the invention, the retainer structure pieces 360 and 362 are typically first inserted or top-loaded into the head U-shaped channel 66, as illustrated by an arrow 397, and then into the cavity 78 to dispose the structure 312 adjacent to the inner surface 80 of the head 10. Alternatively, one of the retainer structure pieces 360 is inserted or top-loaded into the channel 66, while the other retainer structure piece 362, is inserted or bottom-loaded into the cavity 78 through the bore 84 (not shown). Another alternative is to insert or upload both pieces 360 and 362 through the bore 84 (not shown).

Figure 34:
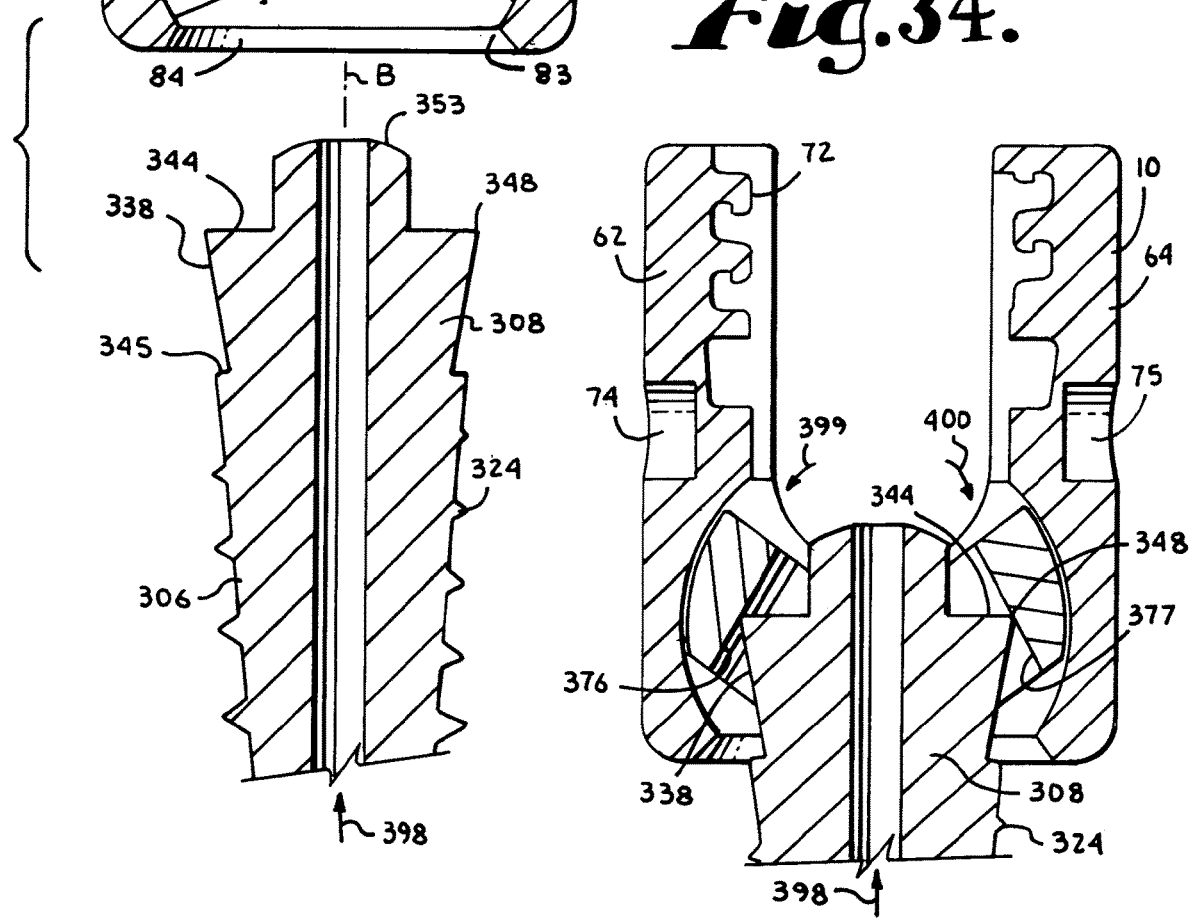
FIG. 34 is an enlarged cross-sectional view of the head, shank and retainer structure pieces, similar to FIG. 33, showing an assembly step according to the invention.

With reference to FIGS. 33 and 34, after the retainer pieces 360 and 362 are disposed in the cavity 78, the shank 304 is inserted or up-loaded into the head 10 through the bore 84. The outer circular edge 348 of the conical surface 338 of the capture structure 308 comes into contact with the sloping inner surfaces 376 and 377 of the respective retainer pieces 360 and 362. Initially all three components: the capture structure 308, and the pieces 360 and 362 may move upwardly as shown by an arrow 398. Then, as the shank 304 continues to move upwardly and into the cavity 78 according to the arrow 398, the retainer structure pieces 360 and 362 pivot about the edge 348 and begin to move downwardly toward the base 60 and outwardly about the capture structure 308 as illustrated by the arrows 399 and 400 in FIGS. 34 and 35.

With reference to FIG. 35, the pieces 360 and 362 continue the downward movement until the bottom surfaces 370 and 371 abut and seat upon the annular seating surface 345 of the shank 304 as illustrated in FIG. 36. Once seated upon the annular surface 345, the retainer structure sloping surfaces 376 and 377 frictionally engage the capture structure conical surface 338.

Subsequent slight downward movement by the shank 304 may be desirable to fully seat the shank/retainer structure assembly in the head cavity 78, with the retainer surfaces 364 and 365 in sliding engagement with the head seating surface 82. The retainer structure 312, now fully seated in the head 10 is coaxially aligned with the shank capture structure 308. At this time, the capture structure 308, the retainer structure 312, the head seating surface 82 and the restrictive neck 83 of the head 10 cooperate to maintain the shank body 306 in rotational relation with the head 10. Only the retainer structure 312 is in slidable engagement with the head spherical seating surface 82. Both the capture structure 308 and the threaded portion of the shank body 306 are in spaced relation with respect to the head 10. An extent of rotation similar to that shown in FIG. 10 with respect to the assembly 1 is also possible with the assembly 301 of the invention. The shank body 306 can be rotated through a substantial angular rotation relative to the head 10, both from side to side and from front to rear so as to substantially provide a universal or ball joint wherein the angle of rotation is only restricted by engagement of the neck 326 of the shank body 306 with the restrictive neck 83 of the head 10.

With reference to FIGS. 12 and 14-16 described earlier herein with respect to the assembly 1, the assembly 301 is similarly screwed into a bone, such as the vertebra 15, by rotation of the shank 304 using the driving tool 31 that operably drives and rotates the shank 304 by engagement thereof with the hexagonally shaped extension or tool engagement head 352 of the shank 304. Preferably, when the driving tool 31 engages the head 352, an end portion thereof abuts and frictionally engages the top surface 344 of the capture structure 308.

Typically, the head 10 and the retainer structure 312 are assembled on the shank 304 before implanting the shank body 306 into the vertebra 15. The steps of preparing the vertebra 15 for bone screw insertion, the bone screw implanting process, the rod reduction and closure top installment processes, and closure top removal process described herein with respect to the assembly 1 may also be similarly performed with the assembly 301. Such processes and above-described apparatus of the assembly 1 are incorporated by reference herein with respect to the assembly 301.

It is to be understood that while certain forms of the present invention have been illustrated and described herein, it is not to be limited to the specific forms or arrangement of parts described and shown.

What is claimed is:
1. A pivotal bone anchor assembly for securing a rod to a bone of a patient, the pivotal bone anchor assembly comprising:
    a shank having an elongate body with a capture structure at a distal end having a spherical shape, the elongate body configured for fixation to the bone;

a receiver having a top portion and a base, the top portion configured to receive the rod, the base having a non-cylindrical internal locking surface at least partially defining a cavity, the receiver having a central bore communicating with the cavity, the cavity communicating with an exterior of the base through a lower opening in the base, the lower opening sized and shaped to receive the capture structure of the shank therethrough;

a retainer structure having at least two discrete retainer parts, each retainer part being positionable within the cavity and having an outer surface and a curved concave inner surface, the retainer parts configured to at least partially surround and capture the capture structure between the curved concave inner surfaces, with the outer surfaces of the retainer parts being frictionally engageable with the internal locking surface of the base, the shank being pivotal with respect to the receiver when the retainer structure is positioned between the capture structure and the internal locking surface during assembly of the pivotal bone anchor assembly and prior to the rod being locked in place within the top portion of the receiver, the retainer structure being configured to at least partially inhibit the shank from moving up out of the retainer structure after the capture structure is captured therein; and a rod-engaging insert positionable in the central bore of the receiver between the rod and the capture structure.

2. The pivotal bone anchor assembly of claim 1, wherein each retainer part is configured for positioning in the cavity prior to the capture structure.

3. The pivotal bone anchor assembly of claim 1, wherein the rod-engaging insert is engageable with each of the retainer parts.

4. The pivotal bone anchor assembly of claim 1, wherein the outer surfaces of the retainer parts and the internal locking surface of the base are complementary.

5. The pivotal bone anchor assembly of claim 1, wherein the outer surfaces of the retainer parts and the internal locking surface of the base are at least partially spherical.

6. The pivotal bone anchor assembly of claim 1, wherein the curved concave inner surfaces of the retainer parts frictionally engage the capture structure.

7. The pivotal bone anchor assembly of claim 1, wherein the at least two discrete retainer parts further comprises a plurality of parts.

8. The pivotal bone anchor assembly of claim 1, wherein the at least two discrete retainer parts further comprises first and second retainer parts.

9. The pivotal bone anchor assembly of claim 8, wherein the second retainer part is a substantial mirror image of the first retainer part.

10. The pivotal bone anchor assembly of claim 8, wherein the first and second retainer parts have different shapes.

11. The pivotal bone anchor assembly of claim 8, wherein the first and second retainer parts are completely separate and spaced-apart from each other in a gapped arrangement when the rod is locked in place within the top portion of the receiver.

12. The pivotal bone anchor assembly of claim 1, wherein the capture structure of the shank has a tool engagement formation disposed thereon adapted for non-slip tool engagement to drive the elongate body of the shank into the bone.

13. The pivotal bone anchor assembly of claim 1, wherein the capture structure of the shank includes at least one inward groove or outward ridge that cooperates with the retainer structure.

14. The pivotal bone anchor assembly of claim 1, wherein the rod-engaging insert is top loaded into the central bore of the receiver.

15. The pivotal bone anchor assembly of claim 1, wherein the shank includes a central opening along an entire length thereof.

16. The pivotal bone anchor assembly of claim 1, wherein the shank includes a top end surface extending above a top surface on the retainer structure when the capture structure of the shank is captured by the retainer structure in the cavity, the top end surface configured to engage the insert positioned in the central bore of the receiver.

17. The pivotal bone anchor assembly of claim 1, wherein each retainer part is sized and shaped to be loadable into the receiver through at least one of an open channel formed in the top portion of the receiver or the lower opening in the base, and wherein the capture structure of the shank is sized and shaped to be loadable into the receiver through the lower opening in the base.

18. The pivotal bone anchor assembly of claim 1, further comprising a closure structure insertable into the receiver, and wherein downward displacement of the closure structure within the receiver results in the outer surface of each retainer part being urged against the internal locking surface of the base, thereby locking the elongate body of the shank in a selected angle with respect to the receiver.

19. The pivotal bone anchor assembly of claim 18, wherein the receiver has upstanding spaced-apart arms defining an open channel, the arms having guide and advancement structures on an inside surface thereof, and the closure structure is configured for downward displacement within the receiver via rotation of the closure structure along the guide and advancement structures.

20. The pivotal bone anchor assembly of claim 1, wherein the cavity includes a width which decreases toward the lower opening in the base.

21. A pivotal bone anchor assembly for securing a rod to a bone of a patient, the pivotal bone anchor assembly comprising:

a shank having an elongate body, a driving tip and a capture structure, the elongate body disposed between the driving tip and the capture structure, the elongate body configured for fixation to the bone, the capture structure having a spherical upper region and a spherical lower region opposite the spherical upper region, the elongate body extending downwardly towards the driving tip from the spherical lower region;

a receiver having a top portion and a base, the top portion defining an open channel configured to receive the rod, the base having an interior surface at least partially defining a cavity of the base, the open channel communicating with the cavity, the cavity communicating with an exterior of the base through a bottom opening in the base, the bottom opening being sized and shaped to receive the capture structure of the shank therethrough; and a retainer structure having first and second retainer pieces, the first retainer piece having a first inner surface and a first outer surface, the second retainer piece having a second inner surface and a second outer surface, the first and second inner surfaces configured for frictional engagement with the capture structure and the first and second outer surfaces configured for frictional engagement with the interior surface that at least partially defines the cavity of the base, the first and second retainer pieces configured to hold the capture structure in the cavity of during angular positioning of the shank relative to the receiver,
wherein the first and second retainer pieces are positionable within the cavity prior to the capture structure.

22. The pivotal bone anchor assembly of claim 21, further comprising an insert positionable in the receiver between the capture structure of the shank and the rod positionable in the open channel.

23. The pivotal bone anchor assembly of claim 21, wherein the first and second retainer pieces have an overlapping relationship with respect to each other.

24. The pivotal bone anchor assembly of claim 21, wherein the first retainer piece includes a recessed portion and the second retainer piece has a projecting portion, the first and second retainer pieces having an overlapping configuration when positioned in the cavity of the base.

25. The pivotal bone anchor assembly of claim 21,
wherein the first and second retainer pieces are sized and shaped to be loadable into the receiver through one of the open channel and the bottom opening, and
wherein the capture structure of the shank is sized and shaped to be loadable into the receiver through the bottom opening in the base.

26. The pivotal bone anchor assembly of claim 21, wherein the first and second inner surfaces of the first and second retainer pieces generally three dimensionally match an outer surface of the capture structure of the shank so as to matingly receive and contact the outer surface of the capture structure between the first and second retainer pieces.

27. A pivotal bone anchor assembly for securing a rod to a bone of a patient, the pivotal bone anchor assembly comprising:
a shank having an elongate body and a capture structure, the elongate body being configured for fixation to the bone;
a receiver having a top portion and a base, the receiver top portion defining a channel to receive the rod, the base having a non-cylindrical internal surface partially defining a cavity, the channel communicating with the cavity, the cavity communicating with an exterior of the base through an opening configured to upward load the capture structure of the shank through the opening; and
a retainer structure having at least two discrete retainer parts, each retainer part having an inner surface and an outer surface, the inner surface configured to be in frictional engagement with the capture structure and the outer surface configured to be in frictional engagement with the non- cylindrical internal surface when the capture structure is captured by the retainer structure, the retainer parts cooperating to prevent the shank capture structure from exiting the receiver cavity through the opening,
wherein the retainer structure is configured for pivotal movement with respect to the receiver prior to the pivotal bone anchor assembly being locked by a closure.

28. The pivotal bone anchor assembly of claim 27, further comprising an insert positionable in the receiver between the retainer structure and the rod.

29. The pivotal bone anchor assembly of claim 28, wherein the insert is configured to set the position of the shank with respect to the receiver prior to insertion of the rod into the receiver channel.

30. The pivotal bone anchor assembly of claim 28, wherein the insert is inhibited from moving upward within the receiver after being positioned therein.

31. A pivotal bone fixation assembly for securing a fixation rod to a bone of a patient, the pivotal bone fixation assembly comprising:
a bone fastener having a head and a bone-engaging portion;
a receiver defining a central through space along a first axis for receiving the bone fastener at a variable angle, the receiver having a non-cylindrical inner surface in a lower portion of the receiver adjacent a bottom opening of the through space; and
a retainer with at least two discrete retainer parts positionable in the receiver lower portion, each retainer part having a planar top surface perpendicular to a second axis of the retainer and an inclined surface with respect to the planar top surface so as to provide clearance space for the at least two retainer parts to pivot relative to each other when installing the head of the bone fastener into the retainer within the receiver through the bottom opening of the receiver through space.

32. The pivotal bone fixation assembly of claim 31, wherein at least one of the two retainer parts includes a recess or notch formed in a surface thereof.

33. The pivotal bone fixation assembly of claim 31, wherein the bottom opening is circular in shape for receiving the head of the bone fastener therethrough.

34. The pivotal bone fixation assembly of claim 31, wherein the at least two retainer parts are configured to move apart with respect to each other when in the receiver so as to capture the head of the bone fastener therein.

35. The pivotal bone fixation assembly of claim 31, wherein the at least two retainer parts are sized and shaped for allowing variable angulation of the bone fastener with respect to the receiver.

36. The pivotal bone fixation assembly of claim 35, wherein the at least two retainer parts are further sized and shaped for preventing removal of the bone fastener from the retainer and the receiver after being captured therein.

37. The pivotal bone fixation assembly of claim 31, wherein the receiver defines an open channel extending along an axis generally perpendicular to the first axis.

38. The pivotal bone fixation assembly of claim 37, wherein the channel is sized and shaped for receiving the fixation rod.

39. The pivotal bone fixation assembly of claim 31, wherein the at least two retainer parts include a first retainer part and a second retainer part.

40. The pivotal bone fixation assembly of claim 39, wherein the first retainer part is configured for mating attachment to the second retainer part about the second axis of the retainer.

41. The pivotal bone fixation assembly of claim 39, wherein the first retainer part cooperates with the second retainer part to surround an outer perimeter of the bone fastener head.

42. A pivotal bone fixation assembly for securing a rod to a bone of a patient, the pivotal bone fixation assembly comprising:
a bone fastener having a head and a bone-engaging portion;
a receiver defining an opening along a first axis for receiving the bone fastener at a variable angle, the receiver having an inner articulation surface at a lower portion of the opening; and first and second retainer parts configured to be coupled to the bone fastener head for movement therewith, the first and second retainer parts being configured to be matingly articulable with the inner articulation surface of the receiver, with at least one retainer part including a notch for receiving a portion of the other retainer part during assembly of the first and second parts with the bone fastener head in the receiver.

43. The pivotal bone fixation assembly of claim 42, wherein the first and second retainer parts are configured to be at least partially overlapping during assembly.

44. The pivotal bone fixation assembly of claim 42, wherein the first retainer part and the second retainer part are configured to cooperate to provide a discontinuous annular curved surface with a three-hundred-and-sixty degree (360°) circumference surrounding the head of the bone fastener so as to capture the head between the retainer parts.

* * * * *

UNITED STATES PATENT AND TRADEMARK OFFICE
CERTIFICATE OF CORRECTION

PATENT NO. : 10,702,309 B2
APPLICATION NO. : 16/544325
DATED : July 7, 2020
INVENTOR(S) : Roger P. Jackson Page 1 of 1

It is certified that error appears in the above-identified patent and that said Letters Patent is hereby corrected as shown below:

In the Claims

- In Claim 21, Column 25, Line 4, delete "of" following 'cavity'.

- In Claim 27, Column 25, Line 54, delete "shank" at the end of the line following 'prevent the'.

- In Claim 42, Column 27, Line 3, delete "bcing" following 'first and second retainer parts' and before 'configured to be'.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*